United States Patent
Swerdlow

(10) Patent No.: US 9,814,876 B2
(45) Date of Patent: Nov. 14, 2017

(54) DETECTION OF DISLODGEMENT OF A DEFIBRILLATION LEAD

(71) Applicant: Lambda Nu Technology LLC, Crystal Bay, MN (US)

(72) Inventor: Charles D. Swerdlow, Los Angeles, CA (US)

(73) Assignee: Lambda Nu Technology LLC, Orono, MN (US)

(*) Notice: Subject to any disclaimer, the term of this patent is extended or adjusted under 35 U.S.C. 154(b) by 0 days.

(21) Appl. No.: 15/013,201

(22) Filed: Feb. 2, 2016

(65) Prior Publication Data
US 2016/0375239 A1   Dec. 29, 2016

Related U.S. Application Data

(60) Provisional application No. 62/231,087, filed on Jun. 25, 2015, provisional application No. 62/283,104, filed on Aug. 21, 2015.

(51) Int. Cl.
| | |
|---|---|
| *A61N 1/08* | (2006.01) |
| *A61N 1/05* | (2006.01) |
| *A61N 1/39* | (2006.01) |
| *A61N 1/372* | (2006.01) |

(52) U.S. Cl.
CPC .............. *A61N 1/08* (2013.01); *A61N 1/3925* (2013.01); *A61N 1/0563* (2013.01); *A61N 1/37258* (2013.01); *A61N 1/3956* (2013.01)

(58) Field of Classification Search
CPC .............. A61N 1/37258; A61N 1/3925; A61N 1/3956; A61N 1/0563; A61N 1/08
See application file for complete search history.

(56) References Cited

U.S. PATENT DOCUMENTS

| | | | |
|---|---|---|---|
| 5,405,363 | A | 4/1995 | Kroll et al. |
| 5,545,186 | A | 8/1996 | Olson et al. |
| 5,713,932 | A | 2/1998 | Gillberg et al. |
| 5,755,736 | A | 5/1998 | Gillberg et al. |
| 6,259,947 | B1 | 7/2001 | Olson et al. |
| 6,980,860 | B2 | 12/2005 | Stadler et al. |
| 7,333,855 | B2 | 2/2008 | Gunderson et al. |

(Continued)

OTHER PUBLICATIONS

Iwasawa J, et al. "Discrimination algorithm of an implantable cardioverter defibrillator in a case with a lead dislodgement". Heart Rhythm. vol. 11, 2014, pp. S491-S492.

(Continued)

*Primary Examiner* — Alyssa M Alter
(74) *Attorney, Agent, or Firm* — Patterson Thuente Pedersen, P.A.

(57) ABSTRACT

Dislodgement of a defibrillation lead from the right ventricle to the right atrium is a rare complication associated with implantable cardioverter-defibrillators. However, such dislodgement deserves attention out of proportion to its low incidence because of the possibility to cause fatal proarrhythmia. Various embodiments are directed to algorithms for detecting lead dislodgement, including a primary algorithm that operates during baseline rhythm and a secondary algorithm that operates during detection of ventricular tachycardia or ventricular fibrillation to identify lead dislodgement during atrial fibrillation.

25 Claims, 12 Drawing Sheets

(56) References Cited

U.S. PATENT DOCUMENTS 8,781,585 B2 7/2014 Gunderson et al.
2014/0018873 A1* 1/2014 Gunderson .......... A61N 1/3702
607/17

OTHER PUBLICATIONS

Ruiz-Salas A, et al. "Inappropriate shock due to late dislocation of electrode. International Journal of Cardiology". vol. 199, 2015, pp. 229-231.
Veltmann C, et al. "Fatal inappropriate ICD shock". J. Cardiovasc. Electrophysiol. vol. 18(3), 2007, pp. 326-328.

* cited by examiner

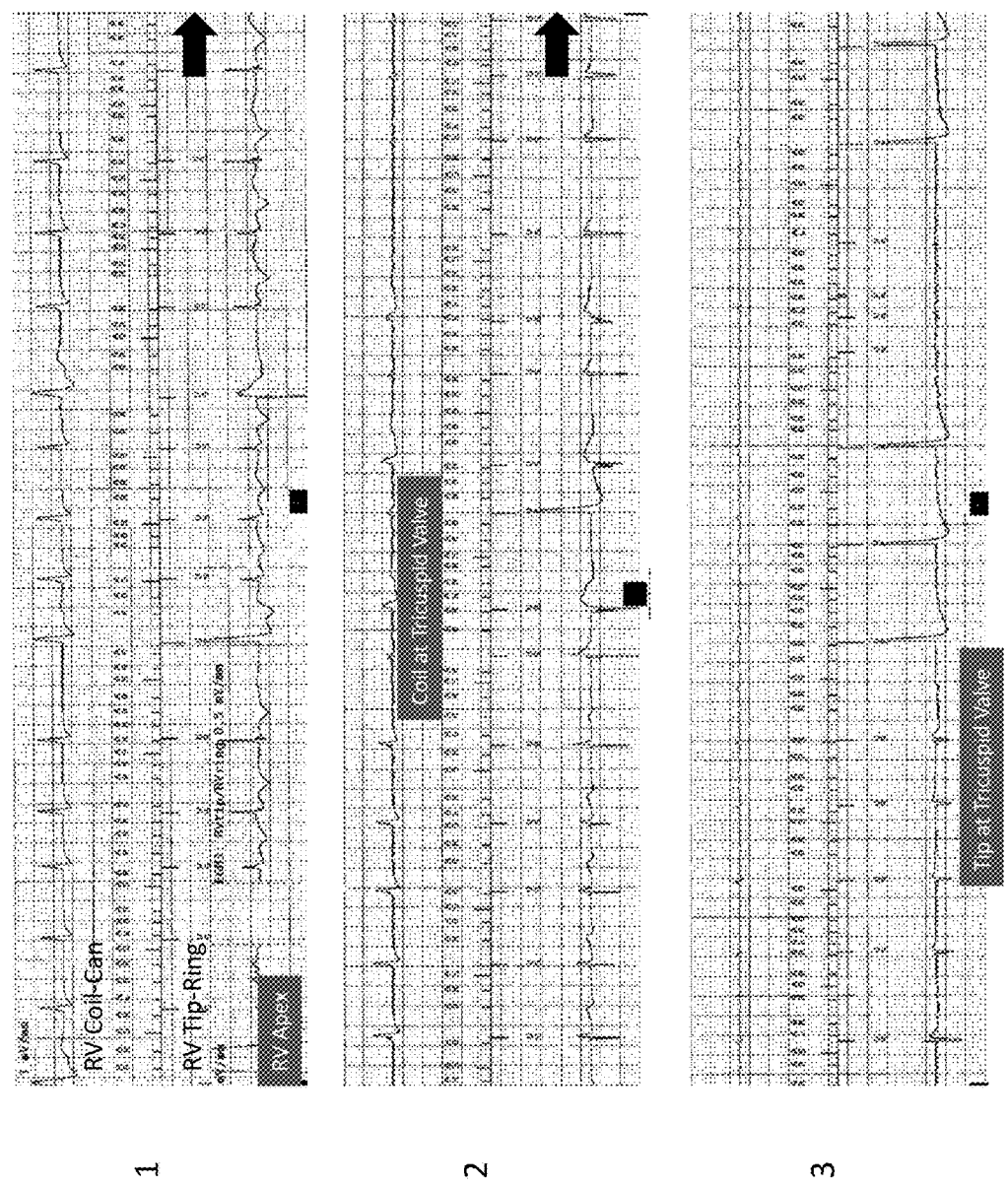
Fig. 2A Simulated RV Lead Dislodgment to RA (Panels 1-3)

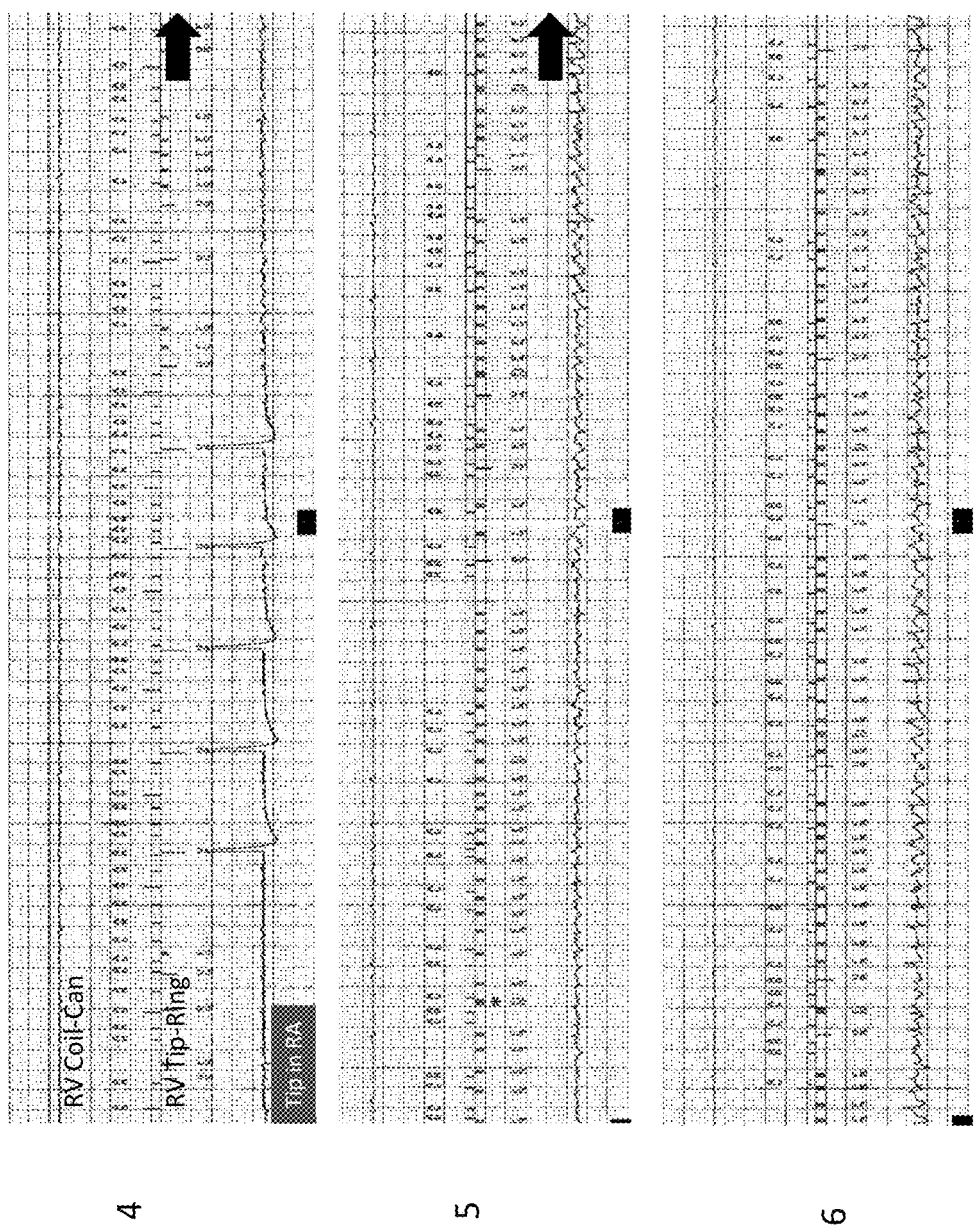

From Ruiz-Salas A, Datino T, Peña-Hernández J, Calvo D, Alzueta J. Inappropriate shock due to late dislocation of electrode. International Journal of Cardiology. 2015

DETECTION OF DISLODGEMENT OF A DEFIBRILLATION LEAD

CROSS-REFERENCE TO RELATED APPLICATIONS

The present application claims the benefit of provisional application No. 62/231,087 filed Jun. 25, 2015 and 62/283,104 filed Aug. 21, 2015, the disclosures of which are incorporated by reference herein.

FIELD OF THE INVENTION

The claimed invention relates generally to implantable medical devices. More particularly, the claimed invention relates to detecting dislodgement of a lead associated with implanted medical devices such as a cardioverter-defibrillator.

BACKGROUND OF THE INVENTION

Implantable cardioverter-defibrillators (ICDs) are used to provide various types of therapy to a cardiac patient, including, for example cardioversion and/or defibrillation. These devices consist of a hermetic housing implanted into a patient and connected to at least one defibrillation electrode and with at least one other electrode e.g., a patch-type electrode, a housing- or can-based electrode, a surface-type electrode, and a stent-based electrode) thereby defining a therapy vector between various pairs of said electrodes. The housing of the ICD contains electronic circuitry for monitoring the condition of the patient's heart, usually through sensing electrodes, and also contains the battery, high voltage circuitry and control circuitry to generate, control and deliver the defibrillation shocks. Typically, one or more specialized defibrillation-type or other transvenous leads are connected to circuitry within the ICD and extend from the housing to one or more defibrillator electrodes proximate the heart. The housing of the ICD may include one or more defibrillation electrodes configured on the exterior of the housing. One example of an ICD is disclosed in U.S. Pat. No. 5,405,363 to Kroll et al., the disclosure of which is hereby incorporated by reference.

Dislodgement of a right ventricular (RV) defibrillation lead to the right atrium (dislodgement to the atrium) is a rare complication associated with ICD therapy. However, such dislodgement deserves attention out of proportion to its low incidence because it may cause fatal proarrhythmia.

Under certain circumstances, dislodgement of an ICD lead into the atrium may cause fatal proarrhythmia in a patient having a normal physiological sinus rhythm. For example, a patient having an ICD may exercise and increase the heart rate to 120 beats-per-minute (bpm) corresponding to an R-R interval of 500 ms and a P-R interval of 200 ms. Both the P-waves and the R-waves are sensed with alternating P-R and R-P intervals of 200 ms (equivalent to 300 bpm) and 300 ms (equivalent to 200 bpm), resulting in detection of ventricular fibrillation (VF) by the implanted cardioverter-defibrillator.

In response to erroneously detecting VF, a shock synchronized to the atrial electrogram (EGM) will likely be delivered by the ICD during the ventricular vulnerable period, 300 ms after the preceding oversensed P-wave. The vector of this shock is from the coil on the right ventricular (RV) lead to the housing or can of the ICD. But because the RV lead has dislodged, the coil of the RV lead is now likely positioned within the right atrium. This vector is sufficient for cardioversion of atrial fibrillation, but not for ventricular defibrillation. Thus the shock will likely be below both the ventricular upper limit of vulnerability, and the defibrillation threshold for this shock vector. Because of this, the shock has a high likelihood of actually inducing VF that the ICD cannot defibrillate.

In another circumstance, dislodgement of an ICD lead into the atrium may cause fatal proarrhythmia in a patient experiencing atrial fibrillation (AF). For example, the high rate of the AF is falsely classified by the implanted cardioverter-defibrillator as VF. In response, a shock synchronized to the atrial electrogram will likely be delivered by the ICD during the ventricular vulnerable period. The vector of this shock is from the coil on the RV lead to the housing or can of the ICD. But because the RV lead has dislodged, the coil of the RV lead is now likely positioned within the right atrium. Because the shock vector is inefficient (right atrium to ICD housing or "can"), the shock's strength will likely be below both the ventricular upper limit of vulnerability and the ventricular defibrillation threshold. Thus the shock has a high likelihood of inducing VF that the ICD cannot defibrillate.

If the inappropriate shock from the dislodged lead defibrillates (cardioverts) the atrium and the ICD then senses only the atrial signals of normal rhythm from its sensing channel, it will classify the shock as successful and, despite ongoing VF, not deliver another shock.

Further, lead dislodgement to the atrium presents a significant risk even if no inappropriate shock is delivered because the ICD is unlikely to defibrillate spontaneous VF with this shock vector and diagnosis of lead dislodgement may be delayed because no present ICD features focus on rapid diagnosis.

Presently, no ICD has implemented any proposed method or algorithm to detect or mitigate lead dislodgement to the atrium. The only proposed solution to the problem of lead dislodgement to the atrium is insufficient. US Published Application No. 2014/0018873 to Gunderson ("the '873 Publication"), teaches an algorithm that withholds therapy in sinus rhythm based on an anticipated pattern of electrical signals on the ventricular near-field (NF) EGM. In general, the term "near-field" refers to an EGM recorded by two or more electrodes, all of which are located in proximity to the source signal for the EGM. As used in ICDs, the NF-EGM ventricular is recorded from two closely-spaced electrodes near the tip of the lead, at least one of which is a small sensing electrode at the tip of the lead. Because these electrodes are closely spaced, their electrical "field of view" is short-range and dominated by the electrical signals originating in myocardium adjacent to the lead tip. The NF-EGM is thus ideal for sensing local myocardial electrical activity, and all ICDs monitor the NF-EGM continuously for the purpose of sensing the cardiac rhythm.

In contrast, a FF-EGM is an EGM recorded by one or more electrodes located at a distance from the source of the EGM. A ventricular FF-EGM records ventricular activation using at least one electrode that is not in a ventricle. As used in ICDs, the ventricular FF-EGM usually refers to an EGM recorded between two or more large, widely-spaced electrodes, used to deliver defibrillation shocks, at least two of which have opposite polarity during the shock and are thus separated in space by a distance of 10 cm or more. The FF-EGM records a more global signal than the NF-EGM, which—as noted previously—records a local signal. The electrodes are commonly used in the art to record the FF-EGM include the right-ventricular defibrillation coil, the housing of the ICD, and (in dual-coil defibrillation leads), the proximal defibrillation coil. Thus, the most commonly-recorded FF-EGM is the "shock" EGM recorded between two or among three widely-spaced, large shock electrodes. However, the EGM recorded between the small electrode at the tip of the defibrillation lead and the housing of the ICD also comprises a FF-EGM, although it is rarely used by ICDs. Under routine operation, the FF-EGM is not monitored continuously or even intermittently during normal rhythm in any ICD. The primary use of the far-field electrical pathway is to deliver high-voltage shocks, not monitor electrical signals. In some ICDs, the FF-EGMs recorded from this electrical pathway is analyzed to perform a secondary function that is activated only after analysis of the sensed NF-EGM indicates that VT or VF is present. This secondary function is to confirm the presence of VT or VF as indicated by the NF-EGM primary sensing channel.

The '873 Publication teaches detection of lead dislodgement to the atrium by the recording of short-long-short-long (S-L-S-L) sequences of intervals between NF-EGM signals. The "short" interval corresponds to the P-R interval; the "long" corresponds to the R-P interval. Additionally, the algorithm requires that each signal have a relatively low amplitude (e.g., 0.5-2.5 mV) and that a zero crossing occurs in the short interval to exclude R-wave double-counting. This algorithm alerts when two such sequences occur. The sensitivity of this pattern for lead dislodgement to the atrium is unknown. Furthermore, there is currently no available evidence that the algorithms described in the '873 Publication perform sufficiently well to be implemented in an implanted ICD.

However, the algorithm described in the '873 Publication would not apply under a number of lead dislodgement to the atrium conditions that do not result in S-L-S-L sequences on the NF-EGM. (1) One example occurs when the atrial rhythm is AF so there are multiple atrial EGMs for each ventricular EGM. Other examples relate to the limited "field of view" NF-EGM. Because this field of view is restricted to local myocardial electrical signals, it does not reliably record signals from two cardiac chambers (atrium and ventricle) simultaneously during the unpredictable conditions of lead dislodgement to the atrium. However, the S-L-S-L sequences on the NF-EGM required by the '873 Publication depend on recording signals from the atrium and ventricle simultaneously. For instance, (2) the lead dislodges but the lead tip remains in the ventricular and does not reach the tricuspid valve so the NF-EGM records a ventricular signal but no atrial signal. (3) The ICD lead dislodges fully into the atrium with the lead tip adjacent to atrial myocardium so that the NF-EGM records an atrial signal but no ventricular signal. (4) The lead is ejected forcefully by ventricular contraction so that its tip moves rapidly from the ventricle into the atrium far from the atrioventricular junction; thus atrial and ventricular EGMs are never both sensed on consecutive cardiac cycles on the so that two S-L-S-L sequences are not recorded; alternatively, a lead dislodging from atrium to ventricle commonly stimulates premature beats, which alters the timing of atrial and ventricular signals so that no S-L-S-L sequence is recorded as the lead traverses the tricuspid valve. (5) As another example, non-capturing ventricular pacing pulses (which are common in lead dislodgement to the atrium) interrupt the S-L-S-L sequence because they are counted as sensed ventricular events. Published examples exist of conditions (1)-(3) during spontaneous lead dislodgements that resulted in unnecessary shocks, and conditions (4)-(5) have been reproduced experimentally. Thus the method of the '873 Publication is insufficient to identify lead dislodgment to the atrium reliably.

Prior art also includes a proposed solution to the reverse problem of atrial lead dislodgement in pacemakers and ICDs that have an atrial lead. U.S. Pat. No. 5,713,932 to Gillberg et al. discloses a method of diagnosing atrial lead dislodgement to the ventricle limited to patients who have intact atrioventricular conduction. Atrial lead dislodgement to the ventricle is diagnosed if the atrial lead is paced and the interval from the atrial pacing pulse to the ventricular NF-EGM is less than the expected delay from atrioventricular conduction.

In view of the above limitations of current approaches, a need remains for an improved method of detecting lead dislodgement.

SUMMARY OF THE INVENTION

In embodiments, the claimed invention is directed to lead dislodgement algorithms (LDAs), including a primary algorithm that operates during baseline cardiac rhythm and a secondary algorithm that operates during detection of ventricular tachycardia (VT) or ventricular fibrillation (VF) to identify lead dislodgement during atrial fibrillation.

In embodiments, the claimed invention may diagnose dislodgement of a right ventricular (RV) defibrillation lead into the right atrium of a patient's heart. In one embodiment, the claimed invention may comprise an algorithm and/or method to detect lead dislodgement based on changes in a ventricular far-field electrogram (FF-EGM) that occur with lead dislodgement to the atrium. In embodiments, lead dislodgement may be detected based on the FF-EGM, based on signals received by the ICD through one or more of the NF and FF channels, based on other information provided to the ICD, based on information contained within an algorithm or other program stored in a memory of the ICD, or combinations thereof. The primary analysis is based on the premise that the earliest EGM changes in the initial dislodgement process occur on the FF-EGM, which has a wide field of view, rather than the NF-EGM used for sensing, which has a narrow field of view. Lead dislodgement to the atrium causes one of two types of changes in the amplitude of the FF-EGM, either an abrupt decrease as the RV coil enters the atrium or a marked increase in beat-beat variability when the coil is in proximity to the tricuspid valve. Additionally, a S-L-S-L sequence may be recorded on the FF-EGM and confirmed by comparison of this sequence with the signal pattern on the NF-EGM. In another embodiment applicable to dual or multichamber ICDs, the claimed invention utilizes analysis of FF-EGMs during atrial-paced rhythm to confirm the S-L-S-L sequence.

In embodiments, the claimed invention is directed to an algorithm and/or method that operates during detection of ventricular tachyarrhythmia (VT) and/or ventricular fibrillation (VF) to identify lead dislodgement during atrial fibrillation. Once activated, the algorithm and/or method suspends detection of VF and provides immediate notification to the patient and/or a remote-monitoring network. Unlike other ICD algorithms that withhold VF therapy, in one embodiment the claimed invention suspends VF detection until an operator reprograms the ICD because once a lead has dislodged, any future failure to satisfy the criteria for lead dislodgement does not necessarily indicate a functioning lead.

In an embodiment, the claimed invention comprises a method of identifying dislodgement of a defibrillation lead from a ventricle of a patient, the lead being operably coupled to an implanted cardioverter defibrillator. The method comprises obtaining a far-field electrogram utilizing one or more electrodes of one or more of the defibrillation lead and the implanted cardioverter defibrillator, at least one of the one or more electrodes configured for delivering a shock therapy, using a processor within the implanted cardioverter defibrillator to determine, based on the far-field electrogram, dislodgement of the defibrillation lead from fixation in the ventricle, and generating an alert that the lead has dislodged in response to using the processor to determine dislodgement of the defibrillation lead.

In an embodiment, the claimed invention comprises an implantable cardioverter defibrillator, configured for coupling to a defibrillation lead. The implantable cardioverter defibrillator comprises a housing, including an electrode, and circuitry contained within the housing. The housing is configured to, upon implant of the implantable cardioverter defibrillator in a patient obtain a far-field electrogram utilizing a therapy electrode on the defibrillation lead and the housing electrode, determine, based on the far-field electrogram, dislodgement of the lead from fixation in a ventricle of the patient, and generate an alert that the lead has dislodged in response to using the processor to determine dislodgement of the lead.

In an embodiment, the claimed invention comprises a method, comprising providing a cardioverter defibrillator to a user, the cardioverter defibrillator including a housing having an electrode, and providing instructions recorded on a tangible medium to the user. The instructions include implanting the cardioverter defibrillator within a patient, coupling the cardioverter defibrillator to a defibrillation lead, and causing the cardioverter defibrillator to initiate operation, the defibrillator programmed to obtain a far-field electrogram utilizing a therapy electrode on the defibrillation lead and the housing electrode, determine, based on the far-field electrogram, dislodgement of the lead from fixation in a ventricle of the patient, and generate an alert that the lead has dislodged in response to using the processor to determine dislodgement of the lead.

In an embodiment, the claimed invention comprises a method of identifying dislodgement of a defibrillation lead from a heart of a patient during atrial tachyarrhythmia, the lead being operably coupled to an implanted cardioverter defibrillator. The method comprises obtaining a plurality of near-field electrograms utilizing one or more electrodes on one or more of the defibrillation lead and the implanted cardioverter defibrillator, using a processor within the implanted cardioverter defibrillator to classify a rhythm of the heart as ventricular fibrillation based on the near-field electrograms, obtaining a plurality of far-field electrograms utilizing one or more electrodes on one or more of the defibrillation lead and the implanted cardioverter defibrillator, using the processor to determine if a majority of amplitudes of the far-field electrograms are below a first predetermined threshold, using the processor to determine if the remainder of amplitudes of the far-field electrograms are below a second predetermined threshold, the second predetermined threshold being larger than the first predetermined threshold, determining, in response to identifying the rapid intervals on the near-field electrograms and determining a majority of amplitudes of the far-field electrograms are below a first predetermined threshold and the remainder of amplitudes of the far-field electrograms are below a second predetermined threshold, that the patient is experiencing an atrial tachyarrhythmia not ventricular fibrillation, and generating an alert that the lead has dislodged from fixation in a ventricle of the heart in response to determining the patient is experiencing atrial tachyarrhythmia.

Embodiments of the claimed invention diagnose lead dislodgement to the atrium based on changes that occur on the ventricular FF-EGM during or after the dislodgement process. This EGM is recorded between two or among three widely-spaced, large shock electrodes and is thus often referred to as the "shock" EGM. Under routine operation, the far-field channel is used only to deliver high-voltage shocks. The FF-EGM is not currently monitored during normal rhythm in any ICD.

Until the research that forms the basis of the claimed invention, understanding of EGM patterns during lead dislodgement to the atrium was limited by the complete absence of data during the process of dislodgement. The few records of lead dislodgement to the atrium comprise EGM recordings triggered serendipitously by algorithms intended to detect other conditions such as VF. Such recordings are limited to the recording EGMs from lead dislodgements to the atrium that trigger EGM storage based on the algorithm's intended purpose and are triggered an unknown time after the defibrillation lead dislodged.

While there is no known precedent for analyzing the FF-EGM to detect lead dislodgement, the FF-EGM has previously been analyzed to detect lead fractures in at least two instances. U.S. Pat. No. 7,333,855 to Gunderson et al. teaches one method, which has been implemented as the "Lead Noise Algorithm™" by Medtronic Inc. The "SecureSense™ RV Lead Noise Discrimination Algorithm" implemented by St. Jude Medical is a second such method.

These two algorithms have been developed to prevent inappropriate shocks caused by a fracture of a defibrillation lead that has not dislodged, and the algorithms incorporate analysis of the FF-EGM but only when the ICD is detecting VF. Fracture of one of the sensing conductors of a defibrillation lead may result in rapid signals on the NF-EGM sensing channel that are fast enough to be detected as VF.

These prior lead fracture detection algorithms work on a common principle, that a true ventricular rhythm disturbance such as VF produces rapid signals on both the NF-EGM and FF-EGM, but a fracture of a conductor to one of the sensing electrodes produces rapid signals on the NF-EGM but does not alter the normal rhythm on the FF-EGM. Thus, once VF is being detected by routine, continuous sensing of the ventricular NF-EGM, the algorithms activate recording from the FF-EGM. They diagnose lead fracture if rapid signals consistent with VF occur only on the NF-EGM but not on the FF-EGM.

Neither of the above lead fracture detection algorithms is designed to detect lead dislodgement to the atrium, and neither algorithm could be suitably modify for such a purpose. For example, one major common limitation for the use of lead fracture detection algorithms to detect lead dislodgement to the atrium is based on their design principle: the lead fracture algorithms function only during brief periods when VF is being detected, but lead dislodgements almost always occur when baseline rhythm is being monitored. Thus neither lead fracture detection algorithm will be activated during the vast majority of occurrences of lead dislodgement to the atrium.

BRIEF DESCRIPTION OF THE DRAWINGS

The invention may be more completely understood in consideration of the following detailed description of various embodiments of the invention in connection with the accompanying drawings, in which:

FIG. 2A is an electrocardiogram readout depicting simulated right ventricular lead dislodgement to the atrium in atrial fibrillation;

FIG. 2B is a continuation of the electrocardiogram readout of FIG. 2A;

Figure 1:
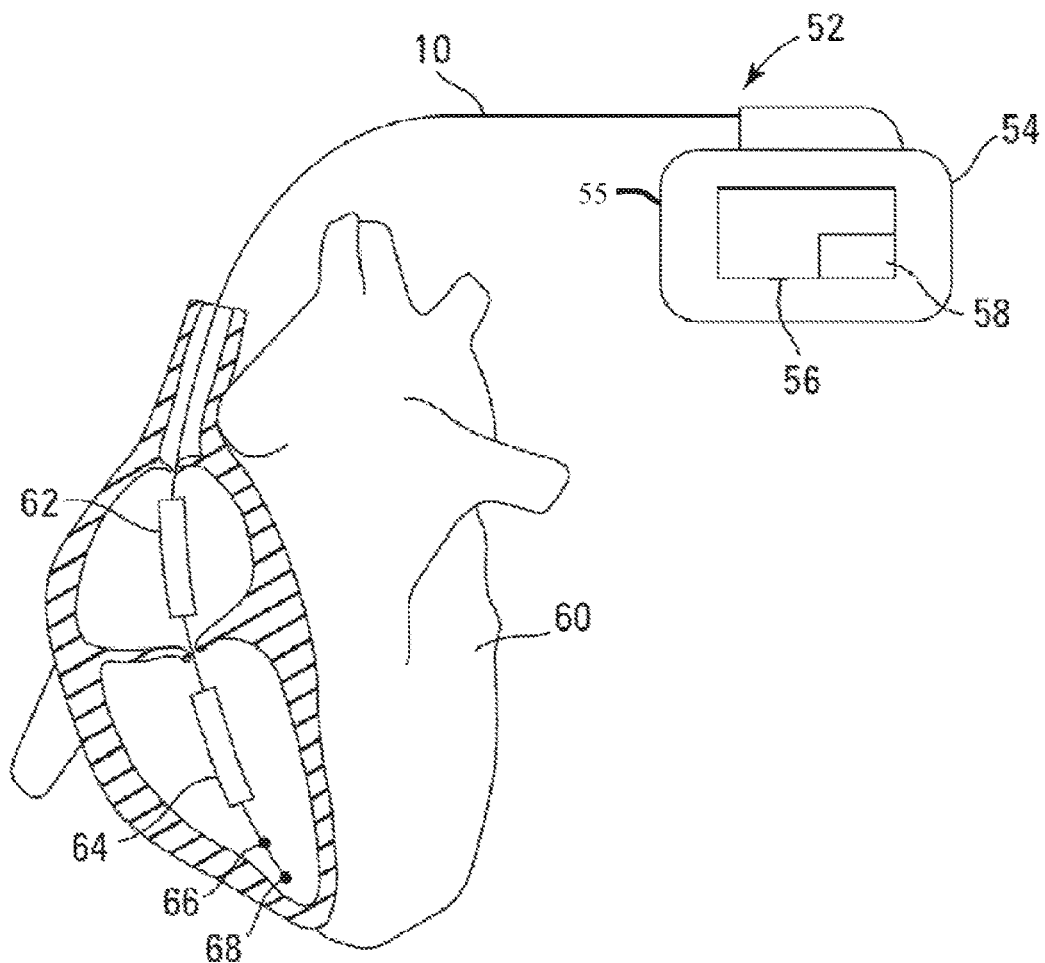
FIG. 1 is a perspective view depicting an implanted cardioverter defibrillator according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

The embodiments of the claimed invention provide methods and apparatus for detecting dislodgement of a lead associated with an ICD.

Referring now to FIG. 1, an ICD 52 is depicted, including an housing or can 54, can electrode 55, inner circuitry 56 including necessary processors, memory and software, a battery 58, and other necessary components as known in the art. Housing 54 may also be referred to as pulse generator 54. Electrode 55 may be on the surface of housing 54, on or part of the header, or other configurations as generally known in the art. Connection is made to a heart 60 via a lead 10. The lead 10 may include a proximal defibrillation coil 62, and a distal defibrillation coil 64. With lead 10 properly implanted and secured within heart 60, coil 62 is configured to be positioned in or near the right atrium and/or superior vena cava, and coil 64 is configured to be positioned in the right ventricle. Coil 62 may alternately be referred to as an SVC coil, and coil 64 may alternately be referred to as an RV coil. Lead 10 may also include one or more ring electrodes 66 and one or more tip electrodes 68, each of electrodes 66 and 68 configured for pacing and/or sensing. Lead 10 may include fixation means, including passive fixation and/or active fixation means as are generally known in the art. ICD 52 may be coupled to additional leads as desired.

Electrograms (EGMs) may be obtained by sensing between various combinations of electrodes. For example, a far-field electrogram (FF-EGM) may be obtained by sensing between RV coil 64 and can electrode 55. A near-field electrogram (NF-EGM) may be obtained by sensing between tip electrode 68 and RV coil 64.

FIG. 2A depicts a continuous FF-EGM recording during a lead dislodgement to the atrium in a patient with AF. The lead dislodgement was simulated by pulling defibrillation lead 10 back from the RV apex to the RA. ICD 52 was set to operate with the following parameters: Medtronic Lead Noise Algorithm on; detection of VF enabled with detection interval of 320 ms; number of intervals to detect and redetect VF set at 18/24 and 12/16; and therapies disabled. FF-EGM and NF-EGM are depicted in FIG. 2A with atrial and ventricular markers.

At the start of Panel 1, the tip of lead 10 is in the right ventricular apex of heart 60 with the fixation screw extended but not fixed. The amplitude of the FF-EGM is 7 mV peak-peak and 5 mV base-peak. The RV coil 64 reaches the tricuspid valve midway through Panel 2. The amplitude of the FF-EGM shows transient beat-beat variability and then decreases abruptly to 1.5 mV peak-peak and <1 mV base-peak. However, the absolute amplitude of the NF-EGM is essentially unchanged because it remains in the ventricle. Thus the FF-EGM indicates dislodgement of lead 10 before the NF-EGM. Any algorithm that analyzes only the NF-EGM cannot identify lead dislodgement at this point. The amplitude of the NF-EGM does not decrease abruptly until the tip electrode reaches the tricuspid valve at the second beat of Panel 3.

FIG. 2B depicts recordings made with the lead tip and RV coil 64 both positioned in the right atrium. The Medtronic Lead Noise Algorithm does not activate because there is no plausible R wave. Inappropriate detection of VF occurs near the left side of Panel 5, as indicted by the FD (Fast Detection, i.e. ventricular fibrillation detected) marker and asterisk, and repeatedly thereafter. Further, the Medtronic Lead Noise Algorithm does not activate to prevent inappropriate detection of VF, as it triggers to withhold therapy only if it identifies signals consistent with a baseline ventricular rhythm on the FF-EGM. In this case, the FF-EGM shows only rapid, low-amplitude signals of AF. Technically, the algorithm described in the '585 patent requires a plausible R wave (>6x average of the 2 smallest EGMs), and dislodgement to the atrium can be associated with sufficient reduction in the amplitude of the FF-EGM that the algorithm will fail to withhold inappropriate shocks because it cannot identify a plausible R wave.

Figure 3A:
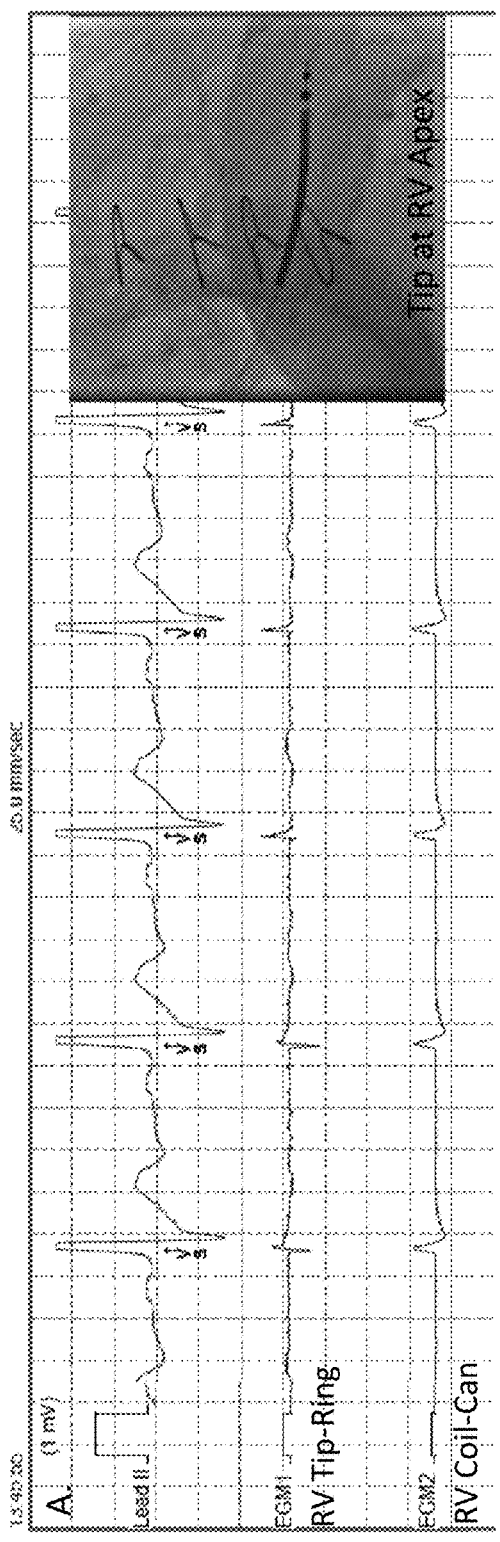
FIG. 3A is an electrocardiogram readout and fluoroscopic image depicting a properly implanted right ventricular lead in sinus rhythm.
Figure 3B:
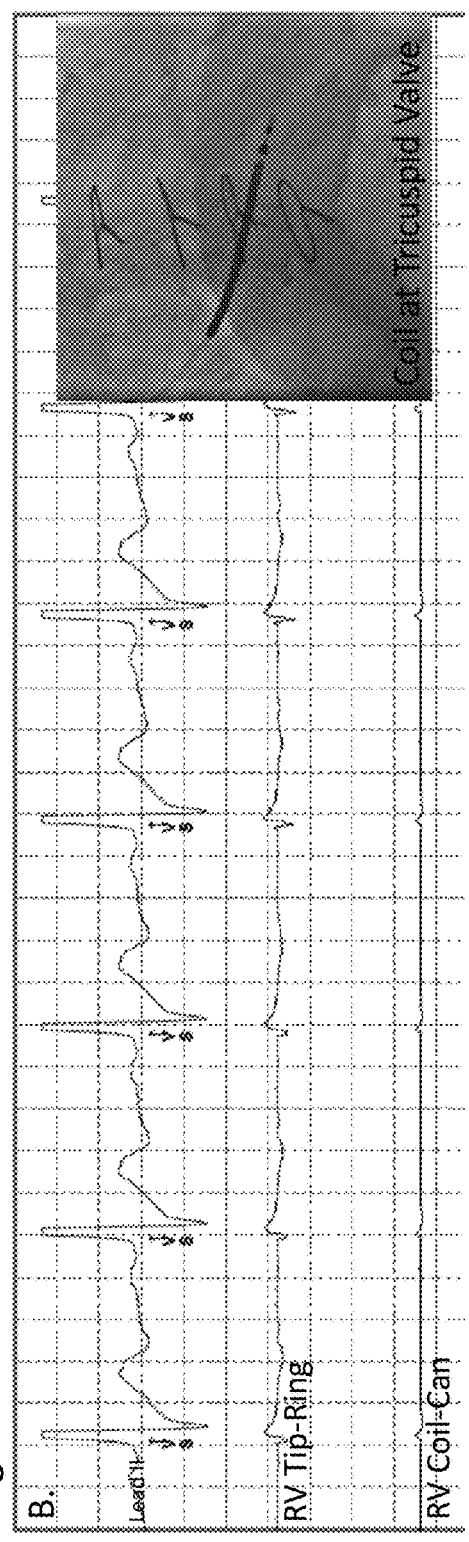
FIG. 3B is an electrocardiogram readout and fluoroscopic image depicting a dislodged right ventricular lead in sinus rhythm

FIGS. 3A-3B depict EGMs and corresponding fluoroscopic images during a simulated dislodgement of lead 10 to the atrium in a patient in sinus rhythm. The fixation screw was extended but not fixed. Each panel shows chest ECG lead II with the NF-EGM and FF-EGM. In FIG. 3A, lead 10 is positioned such that the tip of lead 10 is at the right ventricular apex of heart 60. In FIG. 3B, lead 10 is positioned such that RV coil 64 is at the tricuspid valve. As lead 10 is pulled back further, the amplitude of the FF-EGM decreases much more than the amplitude of the NF-EGM.

Figure 6:
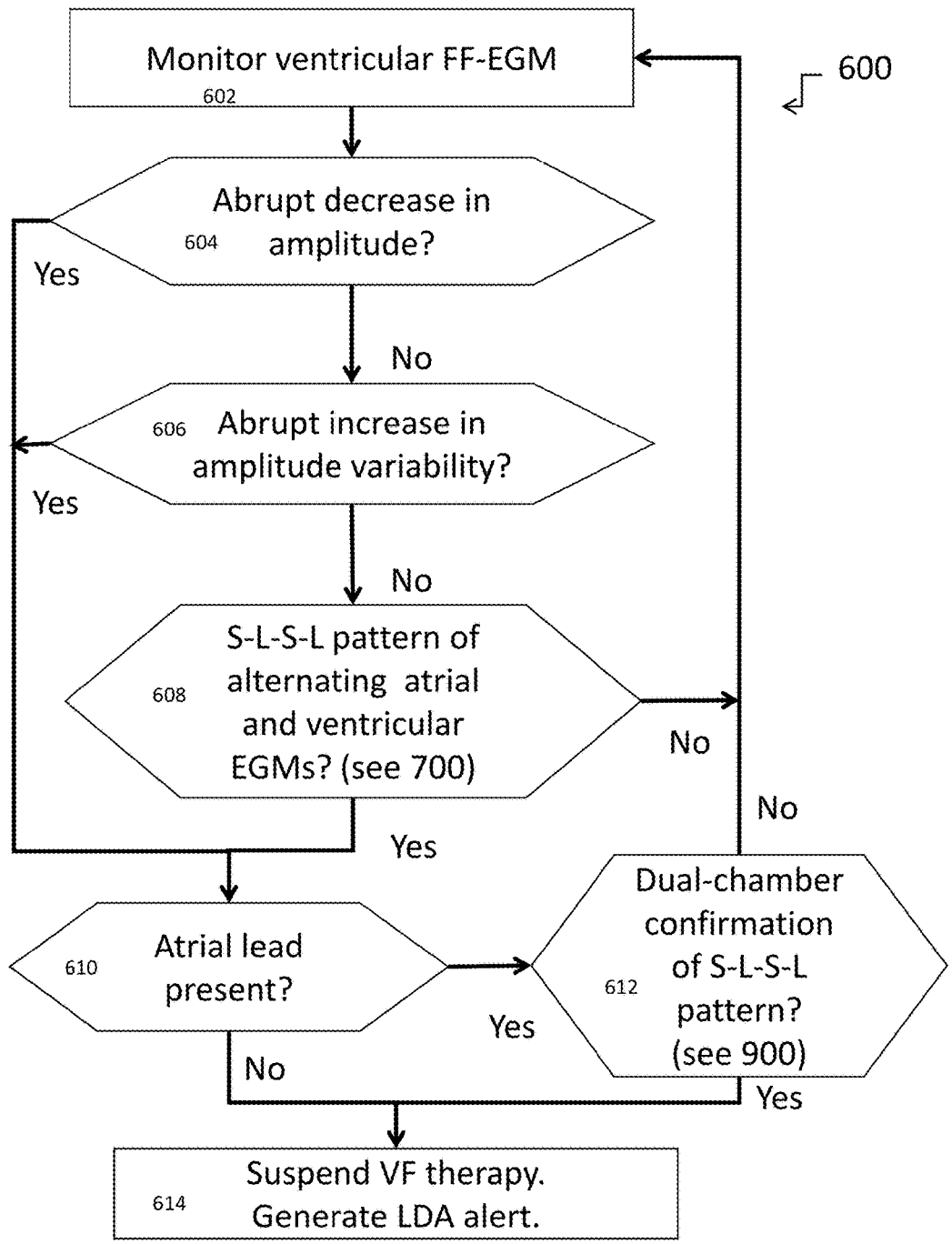
FIG. 6 is a flowchart depicting a method for detecting lead dislodgement to the atrium according to an embodiment.

Thus, these experimental lead dislodgements demonstrate that a change in the amplitude of the FF-EGM is a more sensitive indicator of lead dislodgement to the atrium than changes in the amplitude of NF-EGM both in AF (FIG. 2) and in sinus rhythm (FIG. 3). Based on this discovery, one embodiment of the present disclosure depicted in FIG. 6 is based on the changes in amplitude of the ventricular FF-EGM that occur with lead dislodgement to the atrium.

Figure 4A:
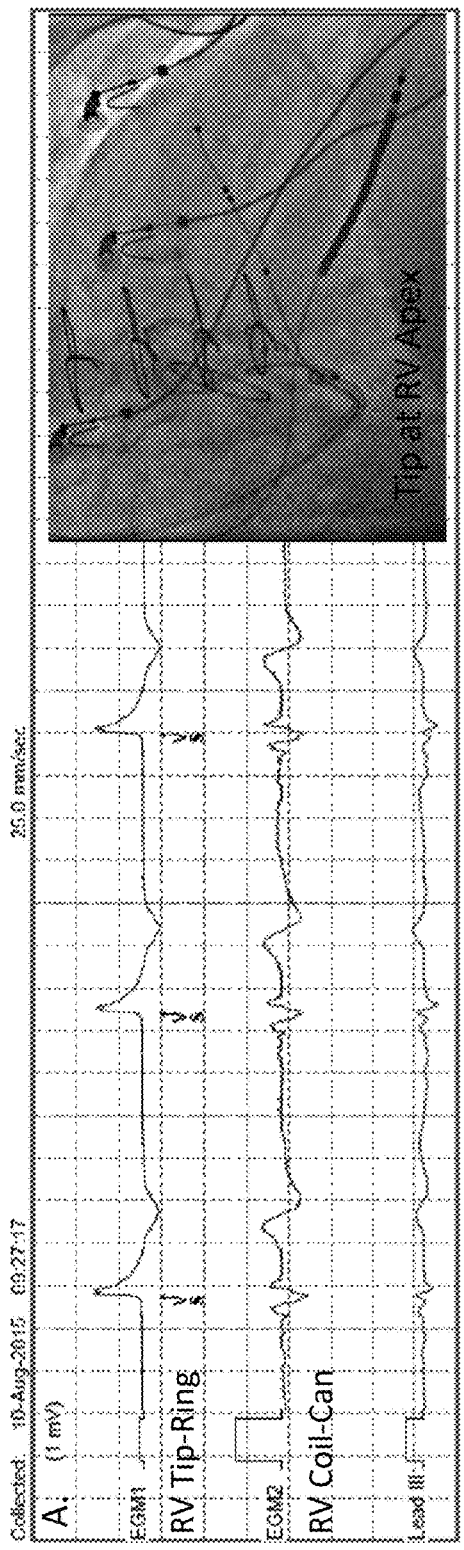
FIG. 4A is an electrocardiogram readout and fluoroscopic image depicting a dislodged right ventricular lead.
Figure 4B:
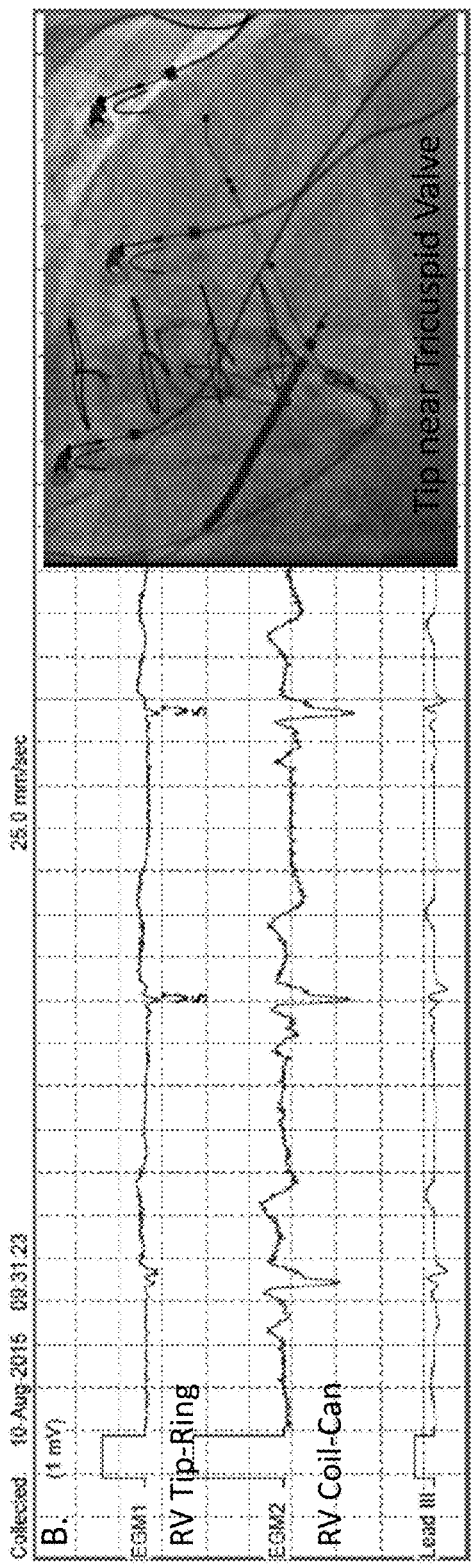
FIG. 4B is an electrocardiogram readout and fluoroscopic image depicting a dislodged right ventricular lead.

However, in a minority of patients, the amplitude of the FF-EGM is so low when lead 10 is properly positioned that it may not decrease further in amplitude with lead dislodgement. FIGS. 4A-4B depicts EGMs and corresponding fluoroscopic images during a simulated dislodgement of lead 10 to the atrium in such a patient in sinus rhythm. Each of FIGS. 4A-4B depict the NF-EGM, FF-EGM, and chest ECG lead III. In FIG. 4A, lead 10 is positioned such that the tip of lead 10 is at the right ventricular apex of heart 60. The NF-EGM is 7.2 mV base-to-peak, but the FF-EGM is only 0.5 mV base-to-peak (0.8 mV peak-peak). In FIG. 4B, lead 10 is positioned such that the tip of lead 10 is on the ventricular side of the tricuspid valve. The NF-EGM has decreased markedly to 0.7 mV base-to-peak, but the already low amplitude of FF-EGM has not changed significantly (0.5 mV base-to-peak, 0.8 mV peak-to-peak). However, the FF-EGM shows the S-L-S-L sequence taught by the '873 application for the NF-EGM. Thus, when the baseline amplitude of the FF-EGM is sufficiently low that a decrease in amplitude may not be detected reliably, the disclosed methods search for the S-L-S-L sequence on the FF-EGM.

Figure 5:
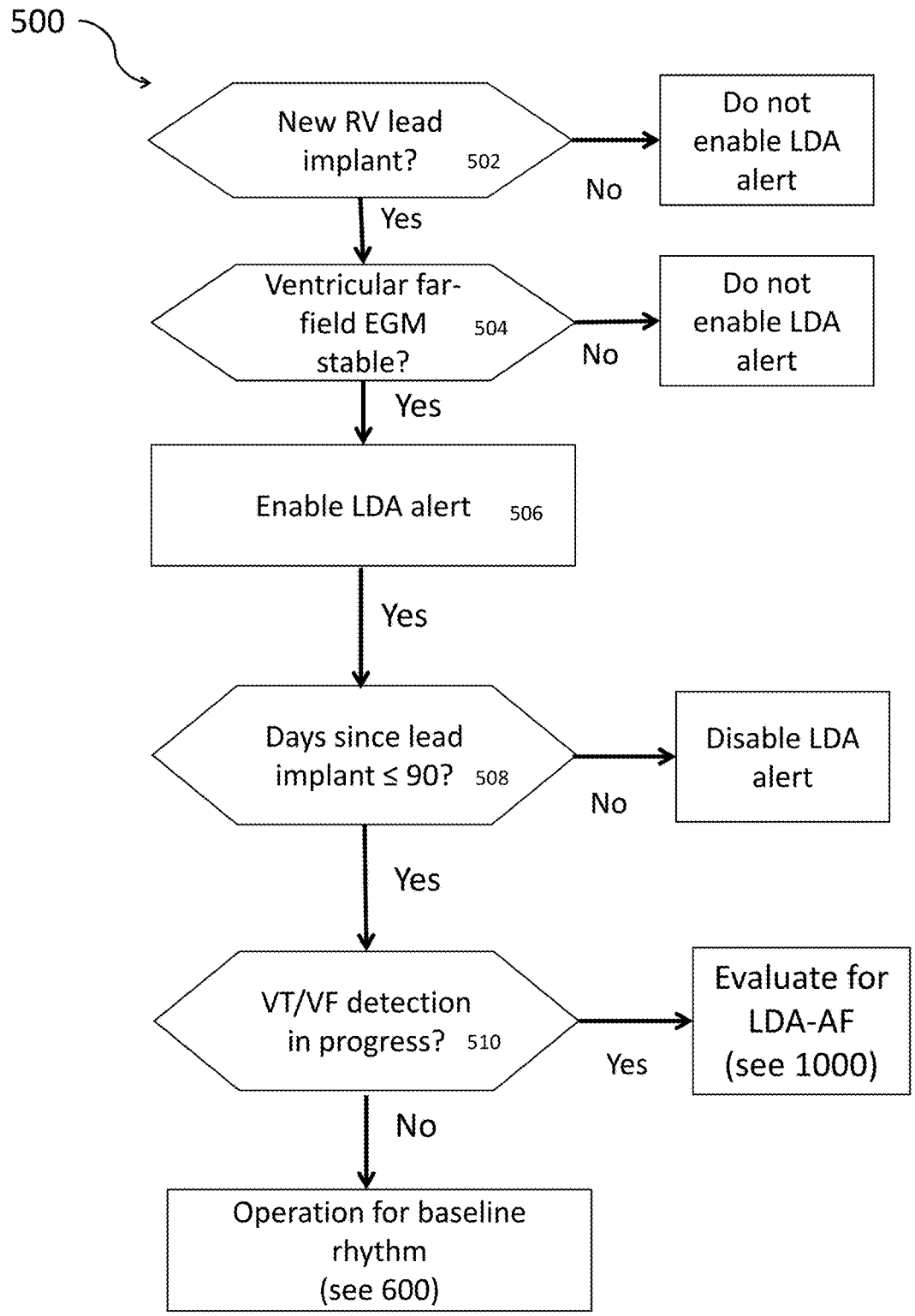
FIG. 5 is a flowchart depicting a method of determining whether or not to enable lead dislodgement to the atrium alerts according to an embodiment.

FIG. 5 depicts a flowchart of a method 500 for determining whether to activate detection for lead dislodgement to the atrium. Optionally, a feature can be added to the initialization procedure for new ICD pulse generators that requires the operator to indicate if a new lead has been inserted. Alternatively, the ICD could detect the presence of a new lead automatically based on the entered serial number or some other feature. Either operator initialization or automated software will trigger recognition of a new lead in 502. Additionally, during the initialization process the operator could indicate if atrial rhythm is long-standing, persistent AF. In such patients, optionally, the S-L-S-L patterns are not applied. Thus steps 608-612 in FIG. 6, method 700 in FIG. 7 and method 900 in FIG. 9 (all discussed in detail below) are omitted.

After lead implant, in 502 the amplitude and duration (width) of the FF-EGM can be measured in 504 until a stable baseline can be established. Measurement may be continuous or intermittent (e.g. every 15-60 minutes) for a period of time (e.g. first 12 hours) or until stable within a predetermined range (e.g. about 20%) for a series of measurements until activated in 506. Unlike the NF-EGM, the FF-EGM becomes stable early after implant because it is not altered by maturation at the electrode-myocardial interface. While it is subject to moderate postural changes in amplitude, these do not occur on a beat-beat basis.

Once activated, the ICD need not monitor for lead dislodgement to the atrium at all times. For example, the algorithm may be activated continuously for the first 24 hours after implant at 506. Subsequently, lead dislodgement to the atrium monitoring may be continuous or intermittent (e.g. every 2-4 hours), provided that the ventricular FF-EGM meets the stability criteria discussed above, at 504. Monitoring for lead dislodgement to the atrium may be triggered in response to internal device events. One such event may comprise sensing a sufficient number of rapid or extremely rapid ventricular events in a short time interval, even if detection of VF does not occur. A further exemplary triggering event may be related to the RV pacing threshold, such as an abrupt increase in RV pacing threshold, which is measured routinely every 6-24 hours. In another example, routine measurement of RV pacing threshold is replaced by repeated measurements (e.g. 3-10) over a brief interval (e.g. 1-10 minutes), and lead dislodgement monitoring is triggered by an abrupt increase in pacing-threshold variability.

All lead dislodgement algorithm features can operate for a programmable period after lead dislodgement algorithm is activated at lead implant, nominally about 90 days (e.g., range 30-180 days) at 508. Once programmed ON, the lead dislodgement algorithm can expire after this active period. In this time frame, the risk of lead dislodgement exceeds the minimal risk of missing ventricular fibrillation that has a very-low amplitude FF-EGM both at onset and continuously thereafter. This expiration feature can reduce any possible risk of withholding VF therapy during more than 95% of the service life of ICD generators implanted with new leads, as well as the entire service life of replacement generators, providing the RV lead is not replaced.

When activated, a primary lead dislodgement algorithm operates during baseline rhythm at 506, as further depicted at 600 in FIG. 6. A secondary algorithm can operate during detection of VT/VF at 510 to identify lead dislodgement to the atrium during AF, as further depicted at 1000 in FIG. 10.

FIG. 6 is a flowchart depicting a method 600 for detecting lead dislodgement to the atrium according to an embodiment. The ventricular FF-EGM can be monitored at 602. During the monitoring, the FF-EGM can be checked for an abrupt change in amplitude at 604, an abrupt increase in amplitude variability at 606, or a S-L-S-L sequence of alternating atrial and ventricular EGMs at 608 (described in further detail in FIG. 7 below). Although described in the context of amplitude, it will be understood that method 600 may also be performed by monitoring one or more other parameters of the FF-EGM, including but not limited to polarity, frequency, content, and morphology.

If 604 or 606 occurs and no atrial lead is present, a lead dislodgement alert can be generated and/or VF therapy can be suspended at 614. If an atrial lead is present, and 604, 606, or 608 occurs, the presence of a dual chamber S-L-S-L sequence can be confirmed at 612 (described in further detail in FIG. 9 below) before generating the lead dislodgement alert and/or suspending therapy at 614. In baseline rhythm, the trigger for a lead dislodgement alert may be fulfillment of any one of criteria 604, 606, 608, or 612 fulfillment of a plurality of criteria, or some other combination of criteria. In one embodiment, measurements for the criteria 604, 606 and 608 are repeated before any criterion is judged to indicate a lead dislodgement to the atrium (e.g. a total of 2 or 3 measurements at brief intervals such as 5-60 second intervals), and any of the criteria 604, 606 or 608 can indicate lead dislodgement to the atrium only if a plurality of repeated measurements indicates lead dislodgement.

According to an embodiment, an abrupt decrease in amplitude can be detected at 604 when the amplitude of the FF-EGM decreases significantly in comparison with a previously established baseline. For example, the amplitude may be out of range as detected by methods known in the art that can be similar to that used to trend AV interval as taught by Stadler et al. U.S. Pat. No. 6,980,860, the disclosure of which is incorporated by reference herein. The out of range amplitude at 604 may also be detected if the amplitude differs by more than a predetermined absolute or relative magnitude, such as absolute ≤1 mV or relative 50% of baseline. According to an embodiment, this decrease in amplitude can be detected at 604 if it occurs relatively rapidly (e.g. over a period of hours to days rather than weeks to month).

According to an embodiment, an abrupt increase in the amplitude variability can be detected at 606 when the amplitude varies markedly on a beat-to-beat basis. According to an embodiment, the minimum and maximum amplitude over a series of beats can be compared. According to another embodiment, the average of the two largest amplitudes can be compared to the average of the two smallest amplitudes and increased variability can be detected when the difference exceeds a threshold. According to an embodiment, T-wave oversensing can be excluded on the FF-EGM (algorithmically or otherwise) before detecting amplitude variability. Analysis of the amplitude variability in this way can allow detection of lead dislodgement even when the R waves have relatively-low baseline amplitude (e.g. <5 mV).

According to an embodiment, lead dislodgement can be detected from the FF-EGM if the FF-EGM records both atrial and ventricular EGMs simultaneously via dual-chamber confirmation of the S-L-S-L sequence at 612. The resulting pattern and required time frame for lead dislodgement alert response differ depending on whether the atrial rhythm is sinus/paced or an atrial tachyarrhythmia (exemplified by AF, although it is understood that the same approach applies to other atrial tachyarrhythmias such as atrial flutter and atrial tachycardia).

If an atrial lead is present at 610, additional dual chamber confirmation that the S-L-S-L pattern represents alternating atrial and ventricular EGMs can be found at 612. The details of dual-chamber confirmation are depicted at 900 in FIG. 9 below.

Once lead dislodgement to the atrium is detected, the algorithm may suspend detection of VF and/or provide immediate notification to the patient and/or remote-monitoring network by methods known in the art. Unlike other ICD algorithms that withhold VF therapy, in one embodiment the lead dislodgement algorithm can suspend VF detection until an operator reprograms the ICD. The rationale is that, once a lead has dislodged, a future failure to satisfy the criteria for lead dislodgement does not necessarily indicate the restoration of a functioning lead.

Figure 7:
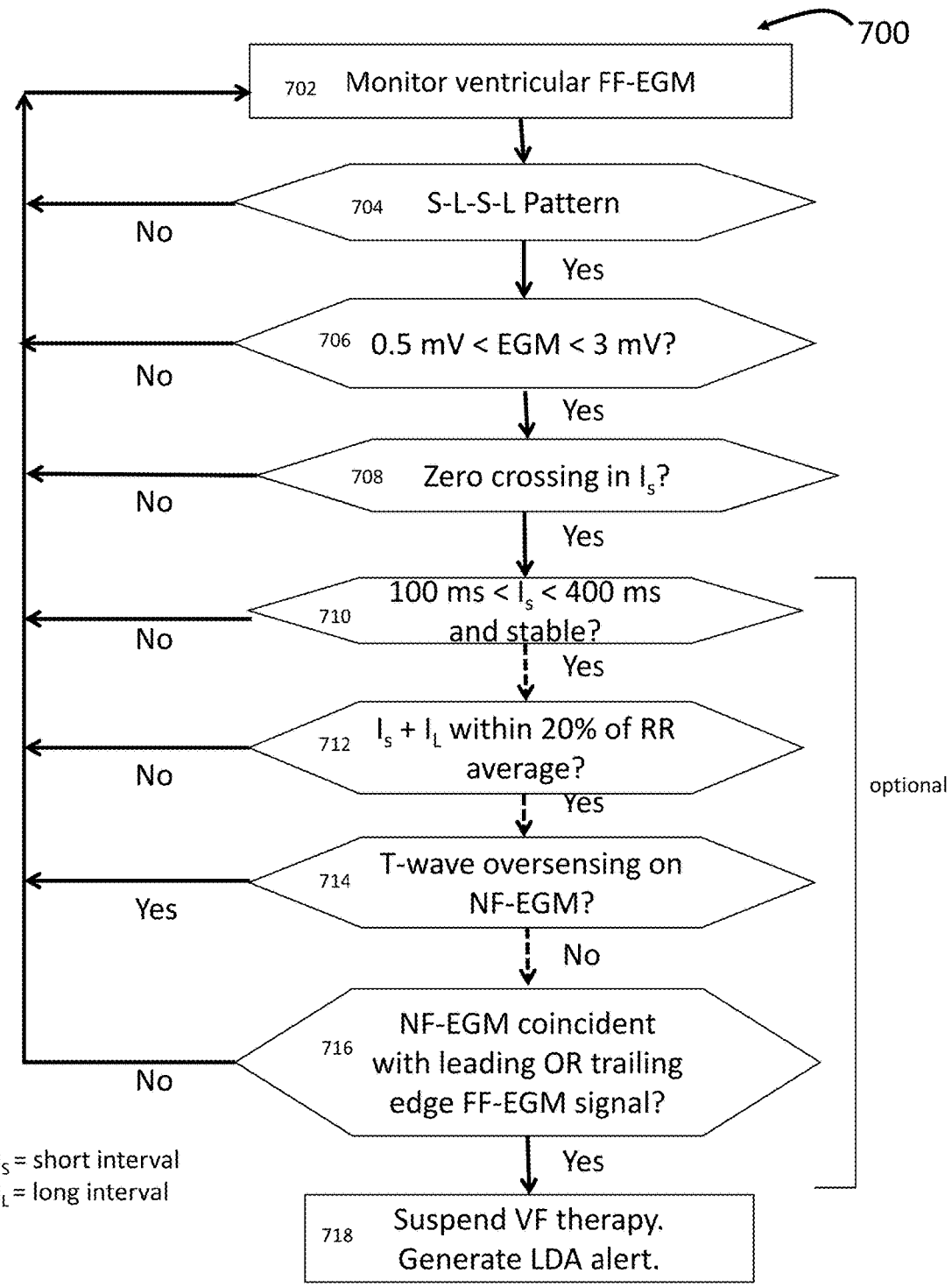
FIG. 7 is a flowchart depicting a method for detecting lead dislodgement to the atrium according to an embodiment.

FIG. 7 is a flowchart depicting a method 700 for detection of lead dislodgement based on detection of a S-L-S-L sequence on the FF-EGM in a single chamber ICD for patients in sinus rhythm, according to an embodiment. This method is applicable to most single-chamber ICD patients because they are in sinus rhythm and have adequate AV conduction (e.g. P-R interval <300 ms). Thus in these patients, recording of both atrial and ventricular EGMs on the same EGM results in the well-known S-L-S-L sequence at normal sinus rates. Method 700 applies this pattern to the far-field ventricular EGM. It is important to recognize that this criterion does not require a priori knowledge that the atrial rhythm is sinus.

According to an embodiment, the ventricular FF-EGM can be monitored at 702. A lead dislodgement alert can be generated and/or VF therapy can be suspended at 718 if an S-L-S-L sequence is detected at 704, all of the FF-EGMs have a relatively low amplitude (e.g. 0.5-3.0 mV) because the coil has dislodged to the atrium at 706, and a crossing occurs in the short interval $I_s$ to exclude R-wave double-counting at 708, for example, as proposed by prior art methods for NF-EGM analysis.

According to embodiments further optional criteria can be applied prior to generating a lead dislodgement alert and/or suspending VF therapy at 718. For example, the method can require the short interval, $I_s$, to be within a plausible range for a P-R interval, for example between 100 and 400 ms at 710. This criterion excludes patterns of ventricular grouped-beating at relatively normal rates (e.g. atrial or ventricular bigeminy, or 3:2 atrioventricular Wenckebach conduction). In embodiments, 710 may also include a criterion that requires each short interval is approximately the same duration (e.g. ±10-20 percent), and/or each long interval is approximately the same duration (e.g. ±10-20 percent). This short-interval stability criterion increases the likelihood that the short interval represents the P-R interval during stable sinus rhythm and may be in addition to other requirements.

In embodiments, method 700 can further require the sum of the successive short and long intervals ($I_s+I_l$) to be within an anticipated range of the baseline R-R interval, for example 20 percent, at 712. This criterion reduces the likelihood of withholding appropriate ICD treatment for rare cases of ventricular tachycardia with alternating R-R intervals. It also further reduces the likelihood of false positive triggers for ventricular bigeminy.

In embodiments, method 700 can further require confirmation by comparison of the index FF-EGM with the NF-EGM. The far-field pattern can be confirmed if T-wave oversensing on the NF-EGM is excluded by methods known in the art at 714 and the NF-EGM has a signal within a short interval (e.g. ±50 ms) of a far-field-EGM at 716. This criterion can be fulfilled by any of these NF-FF EGM comparison patterns:

(1) a single NF signal within a short interval of the leading-edge FF-EGM signal
(2) a single NF signal within a short interval of the trailing-edge FF-EGM signal
(3) two signals, one within a short interval of the leading-edge FF-EGM signal and one within a short interval of the trailing-edge FF-EGM signal.

Step 716 can analyze the temporal relationship between atrial events on the atrial channel at multiple rates and the candidate atrial signal recorded from the ventricular FF-EGM. Atrial events are understood to mean either a sensed atrial EGM, or the atrial pacing pulse. Ventricular lead dislodgement to the atrium can be confirmed by dual-chamber analysis if either the leading or trailing short interval signal of the ventricular FF-EGM is consistently temporally coincident or approximately coincident with the atrial event on the atrial channel both at a baseline rhythm and during pacing at one or more faster rates. Approximate temporal coincidence can be defined as within a predefined interval (e.g. 50 ms) before or after a sensed atrial event, or within that interval after a paced atrial event. Further analysis can be performed during atrial pacing if either the leading or trailing short interval signal of the FF-EGM signal are consistently temporally approximately coincident. The atrium can be paced faster than the baseline rate (e.g. up to 20 bpm faster but slower than the upper rate limit) for about 10 intervals and the temporal relationship can be reassessed. Optionally, this analysis may be performed at a second, even faster, atrial paced rate (e.g. up to 40 bpm faster than the baseline rate but slower than the upper rate limit).

The improved method 700 of the disclosed embodiment differs from the prior approach to detecting lead dislodgement of the '873 Publication in several respects. First, the primary S-L-S-L analysis is performed on the ventricular FF-EGM, not the ventricular NF-EGM as in prior art approaches. The advantage of using the FF-EGM rather than the NF-EGM can be seen in FIG. 8A, where the S-L-S-L sequence is apparent on the FF-EGM but not NF-EGM.

Method 700 applies an amplitude constraint to the FF-EGM at 706 unlike known prior art methods. The advantage of removing this constraint can be seen in the patterns previously discussed with respect to FIGS. 3B and 4B in which lead dislodgement to the atrium with the coil near the tricuspid valve does not cause significant reduction in the amplitude of the NF-EGM, but does on the FF-EGM.

Additionally, prior art methods do not teach the confirmatory steps 714 and 716. In the present embodiment of method 700, the comparison of NF-EGM and FF-EGM in 716 is performed regardless of whether the NF-EGM displays the S-L-S-L sequence, therefore the present embodiment can also identify the patterns in FIGS. 3B and 4B.

Figure 8A:
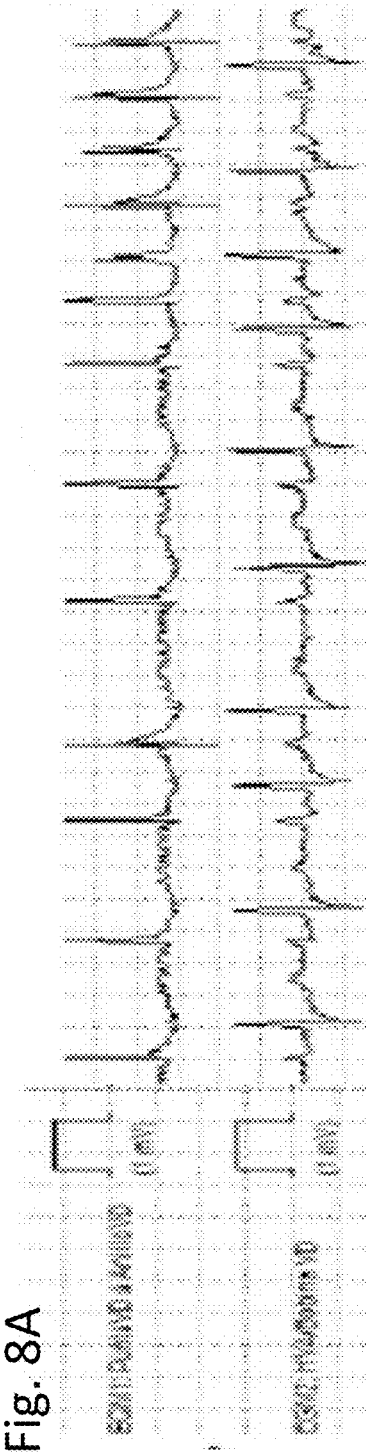
FIG. 8A is an electrocardiogram readout depicting ventricular near-field vs. far-field electrocardiogram correlations in lead dislodgement to the atrium in sinus or atrial paced rhythm.
Figure 8B:
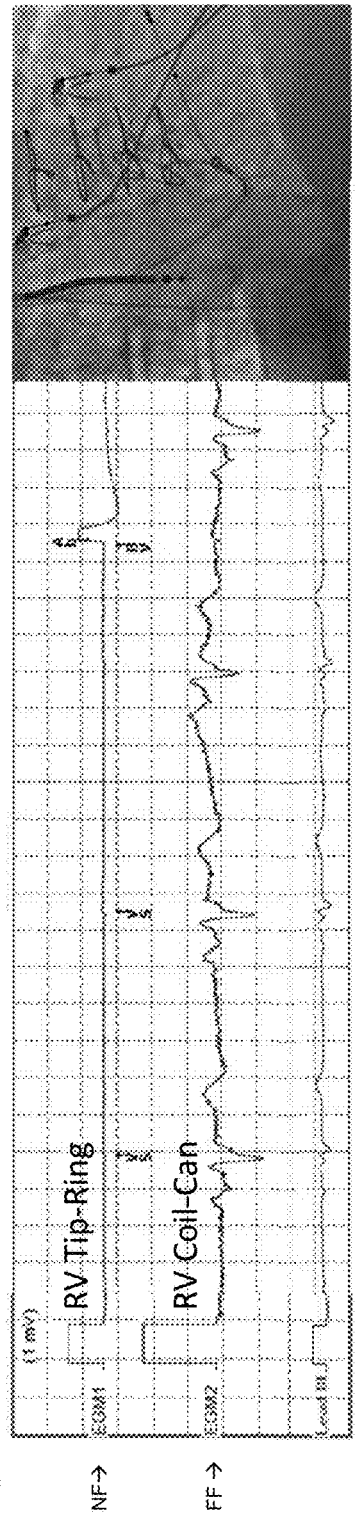
FIG. 8B is an electrocardiogram readout and fluoroscopic image depicting ventricular near-field vs. far-field electrocardiogram correlations in lead dislodgement to the atrium in sinus or atrial paced rhythm.
Figure 8C:
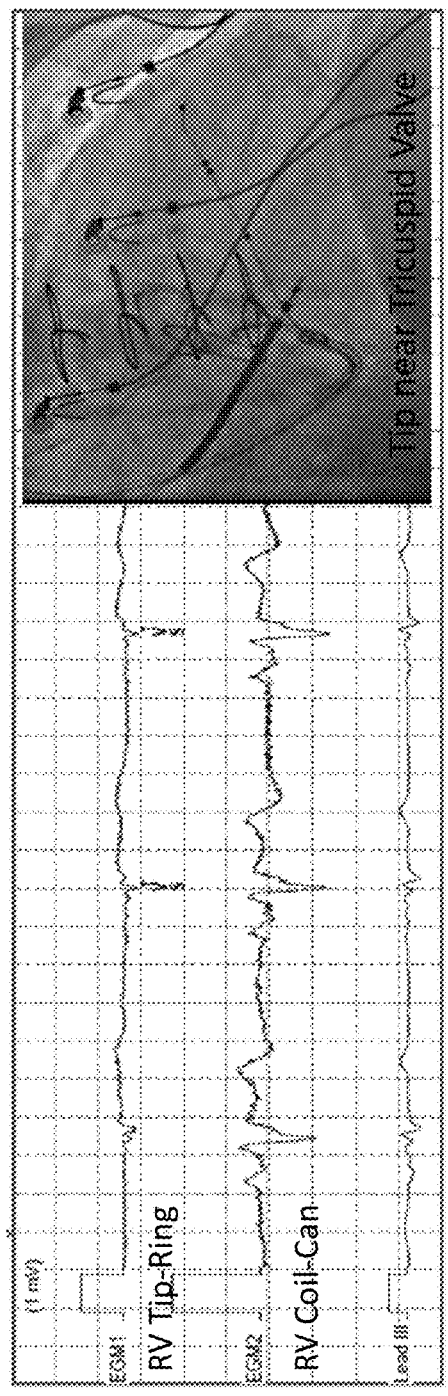
FIG. 8C is an electrocardiogram readout and fluoroscopic image depicting ventricular near-field vs. far-field electrocardiogram correlations in lead dislodgement to the atrium in sinus or atrial paced rhythm.

Further practical advantages of the method 700 over prior art methods are illustrated by FIGS. 8A-8C. FIG. 8A depicts an EGM comparison pattern of a single NF signal within a short interval of the leading-edge FF-EGM signal, wherein the S-L-S-L sequence is present on the FF-EGM but not NF-EGM. This pattern may occur if both RV coil 64 and tip electrode 68 are in the atrium. FIG. 8B depicts another pattern that may occur if tip electrode 68 is in the atrium. In FIG. 8B, tip electrode 68 is free in the atrial cavity so that neither tip electrode 68 nor ring electrode 66 make contact with a wall of the heart; RV coil 64 has pulled back to straddle the junction of the atrium and superior vena cava. The S-L-S-L sequence is present on the FF-EGM, but the NF-EGM shows no cardiac EGM.

FIG. 8C depicts a single NF signal within a short interval of the trailing-edge FF-EGM signal, wherein the S-L-S-L sequence is present on the FF-EGM but not the NF-EGM. The pattern depicted in FIG. 8C may occur if RV coil 64 is in the atrium but RV tip electrode 68 is in the ventricle.

Further, prior art methods may identify the pattern shown in FIG. 8C only if the FF-EGM fulfills an additional relative-amplitude constraint: the signal that ends the short interval (trailing peak) has significantly greater amplitude than the signal that begins the short interval (leading peak, e.g. amplitude ≥1.5 times greater). Method 700 does not require an analysis of the relative amplitudes of signal peaks on the FF-EGM.

Figure 8D:
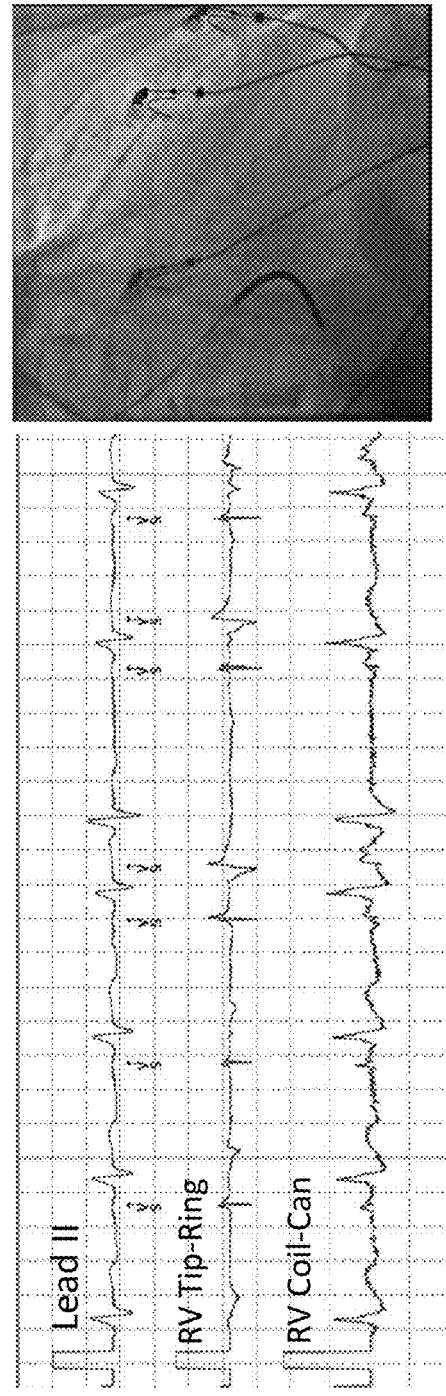
FIG. 8D is an electrocardiogram readout and fluoroscopic image depicting ventricular near-field vs. far-field electrocardiogram correlations in lead dislodgement to the atrium in sinus or atrial paced rhythm.

The advantage of removing this relative-amplitude constraint can be seen in FIG. 8D. In FIG. 8D, the trailing-edge NF-EGM peak never exceeds 1.5 times the magnitude of the leading edge peak. In fact, the leading edge peak exceeds the trailing edge peak for the first, third, and fifth atrial EGMs. In addition, prolonged atrioventricular conduction is common in patients with multichamber ICDs, reversing the S-L-S-L sequence of lead dislodgement to the atrium so that the P wave is the trailing signal of the short interval. The present disclosure permits dual-chamber confirmation in such patients, while prior art methods do not. For this analysis, the confirmation steps at 710 and 712 can be omitted.

Also, method 700 teaches pacing the presumably functioning atrial lead and measuring on the FF-EGM of the potentially dislodged ventricular lead. This can be contrasted to prior art methods which teach pacing the potentially dislodged atrial lead and measuring on the presumably functioning ventricular lead.

Figure 9:
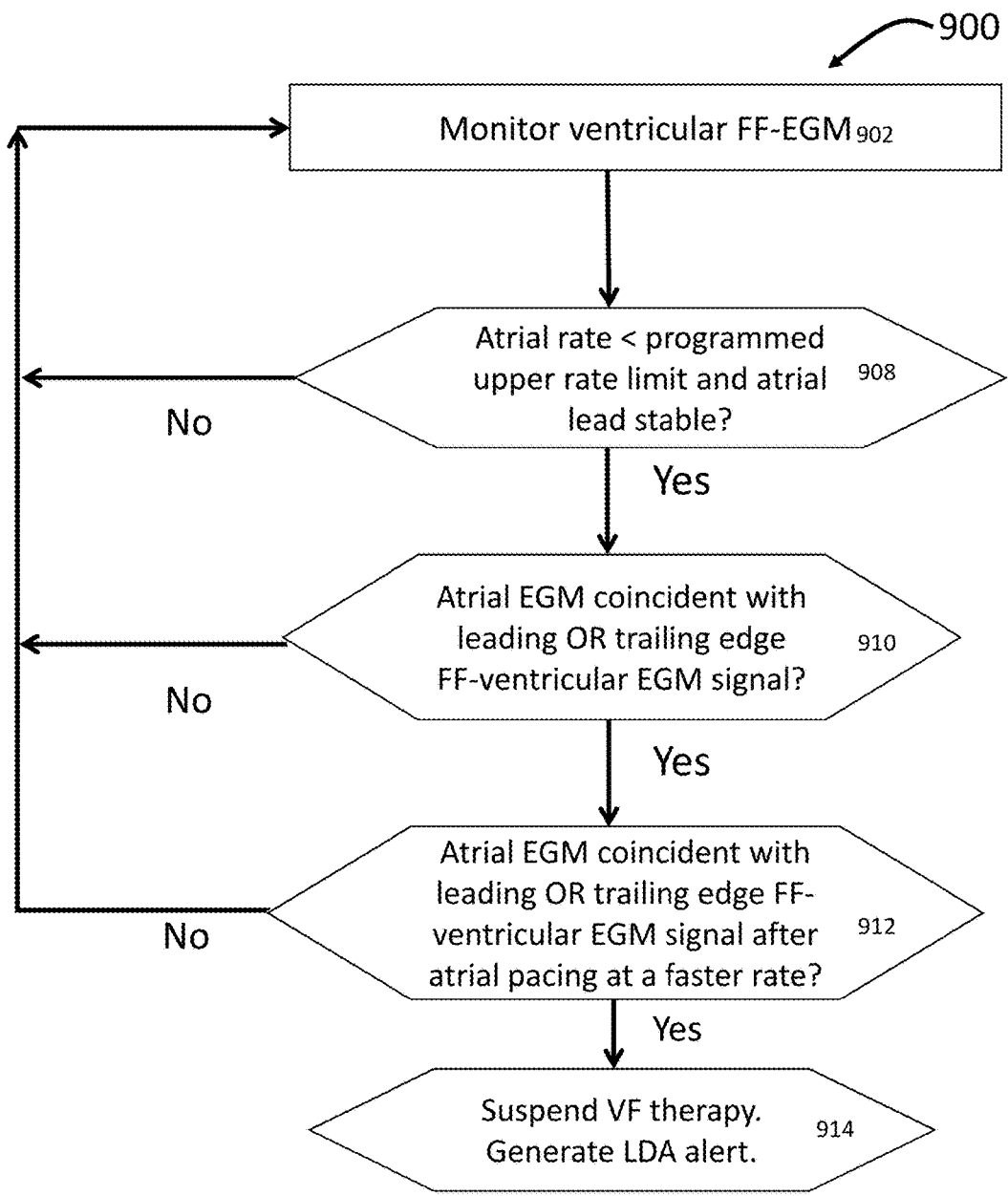
FIG. 9 is a flowchart depicting a method for detecting lead dislodgement to the atrium according to an embodiment.

FIG. 9 is a flowchart depicting a method 900 for additional dual chamber confirmation steps that can be performed in embodiments involving multichamber ICDs if any of the single-chamber lead dislodgement criteria of methods 600 and 700 are fulfilled. Method 900 can analyze the temporal relationship between atrial events on the atrial channel at multiple rates and the candidate atrial signals recorded from the ventricular FF-EGM.

Ventricular lead dislodgement to the atrium can be confirmed by dual-chamber analysis if either the leading or trailing short interval signal of the ventricular FF-EGM is consistently temporally coincident or approximately coincident with the atrial event on the atrial channel both at a baseline rhythm and during pacing at one or more faster rates. Approximate temporal coincidence can be defined as within a predefined interval (e.g. 50 ms) before or after a sensed atrial event, or within that interval after a paced atrial event. Further analysis can be performed during atrial pacing if either the either the leading or trailing short interval signal of the FF-EGM EGM signal are consistently temporally approximately coincident. The atrium can be paced faster than the baseline rate (e.g. up to 20 bpm faster but slower than the upper rate limit) for about 10 intervals and the temporal relationship can be reassessed. Optionally, this analysis may be performed at a second, even faster, atrial paced rate (e.g. up to 40 bpm faster than the baseline rate but slower than the upper rate limit).

In embodiments, dual chamber analysis, method 900 (triggered from step 612) can be used to confirm that either the leading or trailing edge signal of the S-L-S-L pattern represents an atrial EGM. At 908, method 900 confirms that the atrial rhythm is paced, or at a sinus rate slower than the programmed upper pacing rate limit. Mechanical stability and adequate functionality of the atrial lead can be determined by various methods. As an example, the atrial lead is considered stable and functioning if the P-wave amplitude was high enough on the last regularly-scheduled measurement (e.g. ≥1.0 mV), and the last measured atrial pacing threshold was low enough (e.g. ≤3 V) and had not increased substantially since the last measure (e.g. increase less than the greater of 1 V or 50% of the previous measurement). Optionally, this feature can be disabled if spontaneous atrial-lead signals have been confirmed to contain far-field R waves by methods known in the art, for example as described in U.S. Pat. No. 6,259,947 to Olson et al., the disclosure of which is incorporated by reference herein. Further at 908, ICD 52 measures the interval between the atrial pacing stimulus and the FF-EGM signals comprising the leading and trailing edge signals of the short interval.

If the either the leading or trailing short interval signal of the FF-EGM EGM signal are consistently temporally approximately coincident with the sensed atrial event on the atrial channel (e.g. ±50 ms) at 910, further analysis can be performed during atrial pacing at 912.

A lead dislodgement to the atrium alert can be generated at step 914 if the atrial EGM is coincident with the leading or trailing edge of the FF-EGM signal after atrial pacing at a faster rate 912.

Figure 10:
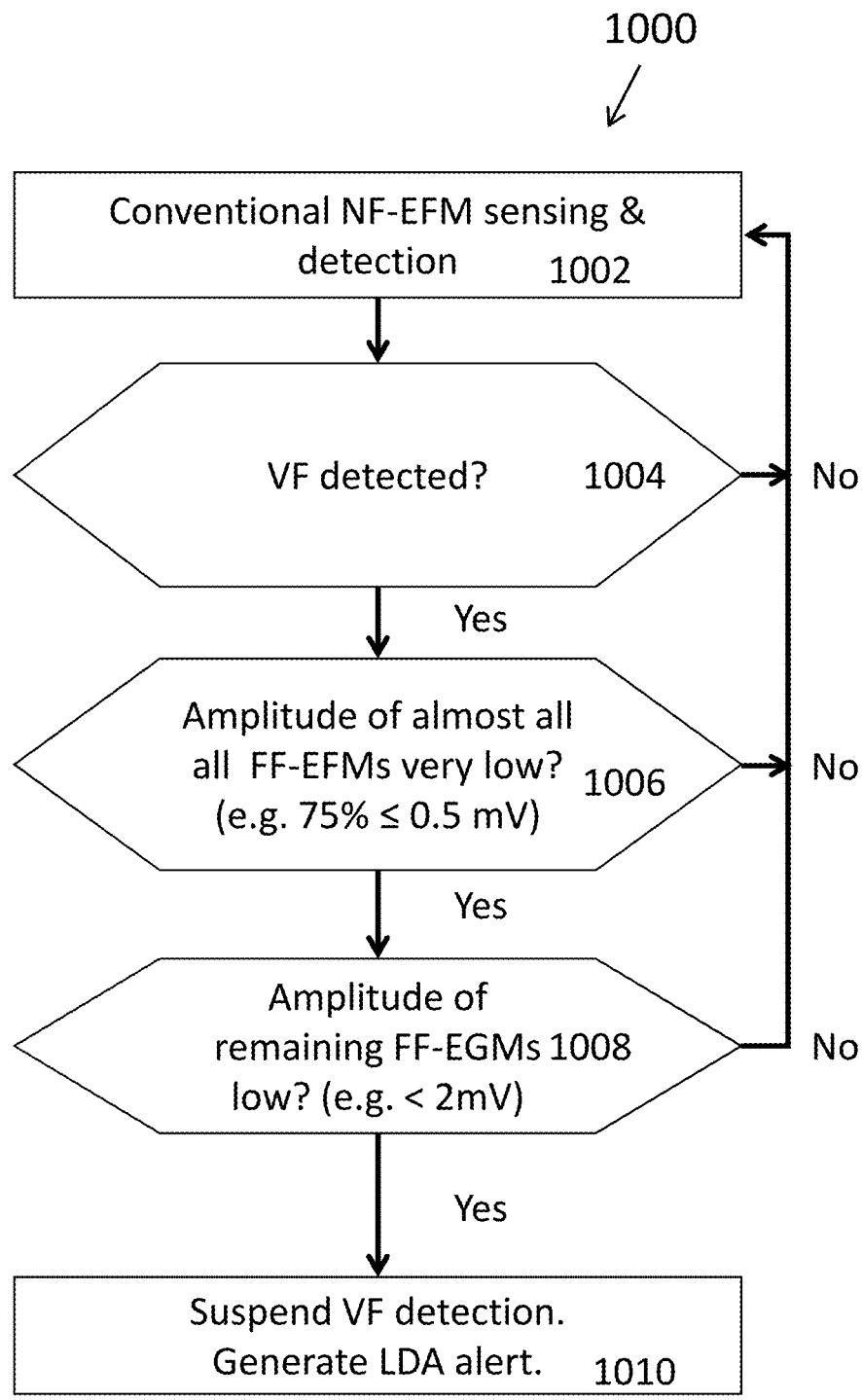
FIG. 10 is a flowchart depicting a method for detecting lead dislodgement to the atrium according to an embodiment.

Referring now to another embodiment, FIG. 10 depicts a method 1000 for detecting lead dislodgement to the atrium during AF. If lead dislodgement to the atrium occurs during AF, false detection by ICD 52 of VF may occur immediately. While this disclosure uses false (inappropriate) detection of VF for illustrative purposes, it is understood that the invention applies equally to inappropriate detection of VT. Thus there is a need for a feature that operates in the event of lead dislodgement to the atrium in AF and prevents immediate inappropriate detection of VF, as well as the resulting inappropriate and dangerous shock.

To achieve this goal, the lead dislodgement detection during AF method 1000 may operate only during detection of VF, independently of the previously described embodiments of lead dislodgement detection alerts. However, if the patient is identified as having long-standing persistent AF at pulse generator initialization, this method may optionally be active continuously. One embodiment depicted in FIG. 10 can be implemented with minimal modifications to prior art related to detection of oversensing related to lead noise from lead fractures (such as taught by the '855 patent). The advantage of operating this feature of the lead dislodgement alert within a lead-noise algorithm is that lead-noise algorithms already operate only during detection of VF.

In one embodiment, detection of VF may be performed according to known methods using the NF-EGM in whole or in part, such as those described in U.S. Pat. No. 5,755,736 to Gillberg et al. or U.S. Pat. No. 5,545,186 to Olson et al., the disclosures of which are hereby incorporated by reference.

According to an embodiment, method 1000 can detect lead dislodgement during AF. Sensing and detection is performed according to known methods at 1002. If VF is detected by ICD 52 at 1004 by inappropriately classifying the heart rhythm as VF, method 1000 checks that the amplitude of a supermajority of FF-EGMs is very low at 1006, and by checking that the amplitude of the remaining FF-EGMs is low 1008. For example, 1006 could determine that at least 75% of FF-EGMs have amplitude ≤0.5 mV and 1008 could determine that all FF-EGMs have amplitude <about 2 mV. If all of criteria 1004, 1006, and 1008 are met, a lead dislodgement alert can be generated at 1010.

The preferred values for 1006 and 1008 were selected because during lead dislodgements in AF most EGMs on the far-field channel will represent atrial depolarization, recorded between a dislodged defibrillation coil with a large surface area exposed to the blood and the remote ICD housing. Their amplitude will be extremely low, lower on a dislodged lead in AF than on a correctly positioned defibrillation lead in early-phase VF. The present method allows for a minority of larger EGMs, corresponding to far-field R waves recorded from dislodged atrial leads in AF. Note that method 1000 removes the requirement of prior art lead noise algorithms for detection of a plausible R wave on the FF-EGM recorded from a defibrillation lead in the RV. In fact, 1008 requires that the larger EGMs be too small to be a plausible R wave recorded from a defibrillation lead correctly positioned in the RV.

The analysis period during which the amplitude of FF-EGMs is calculated could, for example, be a sliding window of twelve sensed beats used by the Lead Noise Algorithm taught in the '855 patent. Other analysis periods could also be used. FF-EGM amplitude can be estimated by various well-known metrics (e.g. maximum, average of peaks, root-mean-square of entire signal, or product of the standard deviation and sum).

The various methods and embodiments described herein may take the form of algorithms, programs, and/or instructions which may be programmed into and/or performed by ICD 52.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the claimed inventions, it is expressly intended that the provisions of Section 112, sixth paragraph of 35 U.S.C. are not to be invoked unless the specific terms "means for" or "step for" are recited in a claim.

The invention claimed is:

1. A method of identifying dislodgement of a defibrillation lead from a ventricle of a patient, the lead being operably coupled to an implanted cardioverter defibrillator, the method comprising:
    obtaining a far-field electrogram utilizing one or more electrodes of one or more of the defibrillation lead and the implanted cardioverter defibrillator, at least one of the one or more electrodes configured for delivering a shock therapy;
    using a processor within the implanted cardioverter defibrillator to determine, based only on the far-field electrogram, dislodgement of the defibrillation lead from fixation in the ventricle; and
    generating an alert that the lead has dislodged in response to using the processor to determine dislodgement of the defibrillation lead,
    wherein the method is performed only for a predetermined amount of time of less than 180 days following implantation of the implanted cardioverter defibrillator.

2. The method of claim 1, wherein the defibrillation lead includes a defibrillation coil electrode and wherein the implanted cardioverter defibrillator includes a housing electrode, the method further comprising:
    obtaining the far-field electrogram utilizing the defibrillation coil electrode and the housing electrode.

3. The method of claim 1, wherein generating the alert comprises suspending one or more operations performed by the implanted cardioverter defibrillator.

4. A method of identifying dislodgement of a defibrillation lead from a ventricle of a patient, the lead being operably coupled to an implanted cardioverter defibrillator, the method comprising:
    obtaining a far-field electrogram utilizing one or more electrodes of one or more of the defibrillation lead and a housing electrode of the implanted cardioverter defibrillator, at least one of the one or more electrodes of the defibrillation lead configured for delivering a shock therapy;
    using a processor within the implanted cardioverter defibrillator to determine, based only on the far-field electrogram, dislodgement of the defibrillation lead from fixation in the ventricle;
    comparing an amplitude of the far-field electrogram to a previously established far-field electrogram baseline;
    determining dislodgement of the lead if the amplitude of the far-field electrogram differs from the baseline by a previously established criteria; and generating an alert that the lead has dislodged in response to using the processor to determine dislodgement of the defibrillation lead.

5. The method of claim 4, wherein the previously established criteria comprises a reduction in magnitude of the amplitude of the far-field electrogram compared to the baseline.

6. The method of claim 4, wherein the previously established criteria comprises a reduction in amplitude of the far-field electrogram of more than 50% compared to the baseline.

7. A method of identifying dislodgement of a defibrillation lead from a ventricle of a patient, the lead being operably coupled to an implanted cardioverter defibrillator, the method comprising:
   obtaining a fir-field electrogram utilizing one or more electrodes of one or more of the defibrillation lead and a housing electrode of the implanted cardioverter defibrillator, at least one of the one or more electrodes of the defibrillation lead configured for delivering a shock therapy;
   using a processor within the implanted cardioverter defibrillator to determine, based only on the far-field electrogram, dislodgement of the defibrillation lead from fixation in the ventricle;
   comparing an amplitude of the far-field electrogram over a series of far-field electrograms;
   determining dislodgement of the lead if a variability of the amplitude of the far-field electrogram over the series of far-field electrograms exceeds a predetermined threshold for variability; and
   generating an alert that the lead has dislodged in response to using the processor to determine dislodgement of the defibrillation lead.

8. The method of claim 7, wherein using the processor further comprises identifying a short-long-short-long sequence in the far-field electrogram to determine dislodgement of the lead.

9. The method of claim 8, wherein using the processor to determine dislodgement of the lead further Comprises confirmation of at least one additional criteria selected from the group consisting of:
   a sum of successive short and long intervals is within a predetermined range of baseline R-R interval,
   at least on short interval is within a predetermined range for a P-R interval,
   each short interval is of approximately the same duration and each long interval is of approximately the same duration, and
   the far-field electrogram is within a predetermined time interval of the near-field electrogram.

10. The method of claim 8, wherein using the processor to determine dislodgement of the lead further comprises confirmation that the far-field electrogram is within a predetermined time interval of the near-field electrogram, the predetermined time interval selected from the group consisting of:
   a near-field electrogram signal is within 50 ms of as leading-edge the short interval of the far-field electrogram signal, and
   a near-field electrogram signal is within 50 ms of a trailing-edge of the short interval of the far-field electrogram signal.

11. A method of identifying dislodgement of a defibrillation, lead from a ventricle of a patient, the lead being operably coupled to an implanted cardioverter defibrillator that is operably coupled to a second lead being implanted in an atrium of the heart, the method comprising:
   obtaining, a first and a second far-field electrogram utilizing one or more electrodes of one or more of the defibrillation leads and a housing electrode of the implanted cardioverter defibrillator, at least one of the one or more electrodes of the defibrillation lead configured for delivering a shock therapy;
   using a processor within the implanted cardioverter defibrillator for:
      determining based on the first far-field electrogram a short-long-short-long sequence in the far-field electrogram that is used to detect dislodgement of the lead; and
      determining based on the second far-field electrocardiogram, whether an atrial rhythm is either paced at or sensed at a sinus rate slower than a programmed upper pacing rate limit;
      measuring an interval between a sensed or paced atrial event and the far-field electrogram signals representative of both a leading edge signal and a trailing edge signal of a short interval; and
      confirming dislodgement of the defibrillation lead if the sensed or paced atrial event is within a predetermined interval of either the leading edge signal or the trailing edge signal; and
   generating an alert that the lead has dislodged in response to using the processor to determine dislodgement of the defibrillation lead.

12. The method of claim 11, wherein the predetermined interval is 50 ms.

13. An implantable cardioverter defibrillator, configured for coupling to a defibrillation lead the implantable cardioverter defibrillator comprising:
   a housing, including an electrode; and
   circuitry contained within the housing configured to, upon implant of the implantable cardioverter defibrillator in a patient and only for a predetermined amount of time following implant of the implanted cardioverter defibrillator:
      obtain a far-field electrogram utilizing a therapy electrode on the defibrillation lead and the housing electrode;
      determine, based only on the far-field electrogram, dislodgement of the lead from fixation in a ventricle of the patient; and
      generate an alert that the lead has dislodged in response to using the processor to determine dislodgement of the lead.

14. The implantable cardioverter defibrillator of claim 13, wherein the therapy electrode on the defibrillation lead comprises a coil electrode.

15. The implantable cardioverter defibrillator of claim 13, wherein the alert comprises suspending one or more operations performed by the implanted defibrillator.

16. An implantable cardioverter defibrillator, configured for coupling to a defibrillation lead the implantable cardioverter defibrillator comprising:
   a housing, including an electrode; and
   circuitry contained within the housing configured to, upon implant of the implantable cardioverter defibrillator in a patient:
      obtain a far-field electrogram utilizing a therapy electrode on the defibrillation lead and the housing electrode;
      compare an amplitude of the far-field electrogram to a previously established far-field electrogram baseline;

determine dislodgement of the lead if the amplitude of the far-field electrogram differs from the baseline by a previously established criteria; and generate an alert that the lead has dislodged in response to using the processor to determine dislodgement of the lead.

17. The implantable cardioverter defibrillator of claim 16, wherein the previously established criteria comprises a reduction in magnitude of the amplitude of the far-field electrogram compared to the baseline.

18. The implantable cardioverter defibrillator of claim 16, wherein the previously established criteria comprises a reduction in amplitude of the far-field electrogram of more than 50% compared to the baseline.

19. An implantable cardioverter defibrillator, configured for coupling to a defibrillation lead, the implantable cardioverter defibrillator comprising:
a housing, including an electrode; and
circuitry contained within the housing configured to, upon implant of the implantable cardioverter defibrillator in a patient:
obtain a far-field electrogram utilizing a therapy electrode on the defibrillation lead and the housing electrode;
compare an amplitude of the far-field electrogram over a series of far-field electrograms;
determine dislodgement of the lead if a variability of the amplitude of the far-field electrogram over the series of far-field electrograms exceeds a predetermined threshold for variability; and
generate an alert that the lead has dislodged in response to using the processor to determine dislodgement of the lead.

20. The implantable cardioverter defibrillator of claim 19, wherein the circuitry contained within the housing is further configured to identify a short-long-short-long sequence in the far-field electrogram to determine dislodgement of the lead.

21. A method, comprising:
providing a cardioverter defibrillator to a user, the cardioverter defibrillator including a housing having an electrode; and
providing instructions recorded on a tangible medium to the user, the instructions including:
implanting the cardioverter defibrillator within a patient;
coupling the cardioverter defibrillator to a defibrillation lead; and
causing the cardioverter defibrillator to initiate operation, the cardioverter defibrillator programmed to:
obtain a far-field electrogram utilizing a therapy electrode on the defibrillation lead and the housing electrode;
determine, based only on the far-field electrogram, dislodgement of the lead from fixation in a ventricle of the patient;
generate an alert that the lead has dislodged in response to dislodgement of the lead being determined; and
obtain the far-field electrogram and determine dislodgement only for a predetermined amount of time following implanting of the implanted cardioverter defibrillator.

22. The method of claim 21, wherein providing the implantable defibrillator to the user comprises causing the implantable defibrillator to be manufactured and made available to the user.

23. A method of identifying dislodgement of a defibrillation lead from a heart of a patient during atrial tachyarrhythmia, the lead being operably coupled to an implanted cardioverter defibrillator, the method comprising:
obtaining a plurality of near-field electrograms utilizing one or more electrodes on one or more of the defibrillation lead and the implanted cardioverter defibrillator;
using a processor within the implanted cardioverter defibrillator to classify a rhythm of the heart as ventricular tachyarrhythmia based on the near-field electrograms;
obtaining a plurality of far-field electrograms utilizing one or more electrodes on one or more of the defibrillation lead and the implanted cardioverter defibrillator;
using the processor to determine if a majority of amplitudes of the far-field electrograms are below a first predetermined threshold;
using the processor to determine if the remainder of amplitudes of the far-field electrograms are below a second predetermined threshold, the second predetermined threshold being larger than the first predetermined threshold;
determining, in response to identifying the rapid intervals on the near-field electrograms and determining a majority of amplitudes of the far-field electrograms are below a first predetermined threshold and the remainder of amplitudes of the far-field electrograms are below a second predetermined threshold, that the patient is experiencing an atrial tachyarrhythmia not ventricular fibrillation; and
generating an alert that the lead has dislodged from fixation in a ventricle of the heart in response to determining the patient is experiencing atrial tachyarrhythmia.

24. The method of claim 23, wherein the first predetermined threshold is 0.5 mV and the second predetermined threshold is 2 mV.

25. The method of claim 23, wherein generating the alert comprises suspending a detection of ventricular tachyarrhythmia operation performed by the implanted cardioverter defibrillator.

* * * * *